US008323643B2

(12) United States Patent
Badalamente et al.

(10) Patent No.: US 8,323,643 B2
(45) Date of Patent: Dec. 4, 2012

(54) METHODS FOR TREATING ADHESIVE CAPSULITIS

(75) Inventors: Marie A. Badalamente, Mt. Sinai, NY (US); Edward Wang, Poluott, NY (US)

(73) Assignee: The Research Foundation of State University of New York, Albany, NY (US)

( * ) Notice: Subject to any disclaimer, the term of this patent is extended or adjusted under 35 U.S.C. 154(b) by 667 days.

(21) Appl. No.: 12/266,090

(22) Filed: Nov. 6, 2008

(65) Prior Publication Data
US 2009/0123454 A1     May 14, 2009

Related U.S. Application Data

(63) Continuation of application No. 11/335,157, filed on Jan. 19, 2006, now abandoned.

(60) Provisional application No. 60/645,772, filed on Jan. 21, 2005, provisional application No. 60/677,440, filed on May 3, 2005, provisional application No. 60/719,470, filed on Sep. 22, 2005.

(51) Int. Cl.
*A61K 38/46* (2006.01)

(52) U.S. Cl. .................. 424/94.67; 435/18; 435/195

(58) Field of Classification Search ................... None
See application file for complete search history.

(56) References Cited

U.S. PATENT DOCUMENTS

| | | | |
|---|---|---|---|
| 5,589,171 A | 12/1996 | Wegman | |
| 5,952,215 A | 9/1999 | Dwulet et al. | |
| 5,989,888 A | 11/1999 | Dwulet et al. | |
| 7,854,929 B2 | 12/2010 | Badalemente et al. | |
| 2007/0224184 A1 | 9/2007 | Badalemente et al. | |

FOREIGN PATENT DOCUMENTS

EP          1433845 A1     6/2004

OTHER PUBLICATIONS

The term "Prevent" definition from online Merriam-Webster dictionary at the web—http://www.merriam-webster.com/dictionary/prevent, pp. 1-2, accessed on May 18, 2011.*
Hutchinson, J.W., et al., "Dupuytren's Disease and Frozen Shoulder Induced by Treatment with a Matrix Metalloproteinase Inhibitor," The Journal of Bone and Joint Surgery 80B(5): pp. 907-908 (1998).
Balci, N., et al., "Shoulder Adhesive Capsulitis and Shoulder Range of Motion in Type II Diabetes Mellitus: Associations with Diabetic Complications," Journal of Diabetes Complications, 13(3): pp. 135-140 (1999), Abstract Only.
Bunker, T.D., "Frozen shoulder: unravelling the enigma", Ann R Coll Surg Engl 79, pp. 210-213, 1997.
Hulstyn, et al., "Adhesive capsulitis of the shoulder", Orthopaedic Review, pp. 425-433, Apr. 1993.
Hannafin, et al., "Adhesive capsulitis, A treatment approach", Clinical Orthopaedics and Related Research, No. 372, pp. 95-109 2000.
Hurst, L.C., et al., "Injectable clostridial collagenase: striving toward nonoperative treatment options for fibroproliferative disorders," available at http://www.aaos.org/research/committee/ research/Kappa/KD2009_Hurst.pdf.
Siegel, L.B., et al., "Adhesive Capsulitis: A Sticky Issue", American Family Physician 59(7), pp. 1843-1852, available at http://www.aafp.org/ afp/990401ap/1843.html, Apr. 1, 1999.
Bains, et al., "Primary frozen shoulder, The untold story!", Journal of Bone and Joint Surgery—British Volume vol. 90-B. Supp_II, 352 (abstract), 2006.
Badalamente et al: "Collagen as a clinical target: Nonoperative treatment of dupuytren's disease" The Journal of Hand Surgery, W.B. Saunders, vol. 27, No. 5, Sep. 1, 2002, pp. 788-798.
Bunker T 0 et al: "The pathology of 1-10 frozen shoulder. A Dupuytren-like disease." The Journal of Bone and Joint Surgery. British Volume Sep. 1995, vol. 77, No. 5, Sep. 1995, pp. 677-683.
Kilian 0 et al: "[The frozen shoulder. 1-10 Arthroscopy, histological findings and transmission electron micrgscopy imaging]" Der Chirurg; Zeitschrift Fur Alle Gebiete Der Operativen Medizen Nov. 2001, vol. 72, No. 11, Nov. 2001, pp. 1303-1308.
Dimarcantonio, T., "Multiple Collagenase Injections Effective, Safe for Treating 'Frozen Shoulder'," ORTHOSuper Site, Retrieved from the Internet: http://www.orthosupersite.com/view.aspx?rid=16738#jump [retrieved on Nov. 8, 2011] (May 2008).

* cited by examiner

*Primary Examiner* — Irene Marx
*Assistant Examiner* — Satyendra Singh
(74) *Attorney, Agent, or Firm* — Mahreen Chaudhry Hoda, Esq.; Carolyn S. Elmore, Esq.; Elmore Patent Law Group, P.C.

(57) ABSTRACT

The invention relates to the discovery that collagenase injections are effective in lyse the collagenous adhesions in the shoulder and treat the disorder, adhesive capsulitis. As such, the invention relates to methods of treating or preventing adhesive capsulitis, or frozen shoulder, in a patient in need of such treatment comprising injecting or otherwise delivering an effective amount of collagenase to the collagenous adhesions in the shoulder. The invention also relates to the use of collagenase in the manufacture of a medicament to treat adhesive capsulitis.

8 Claims, 34 Drawing Sheets

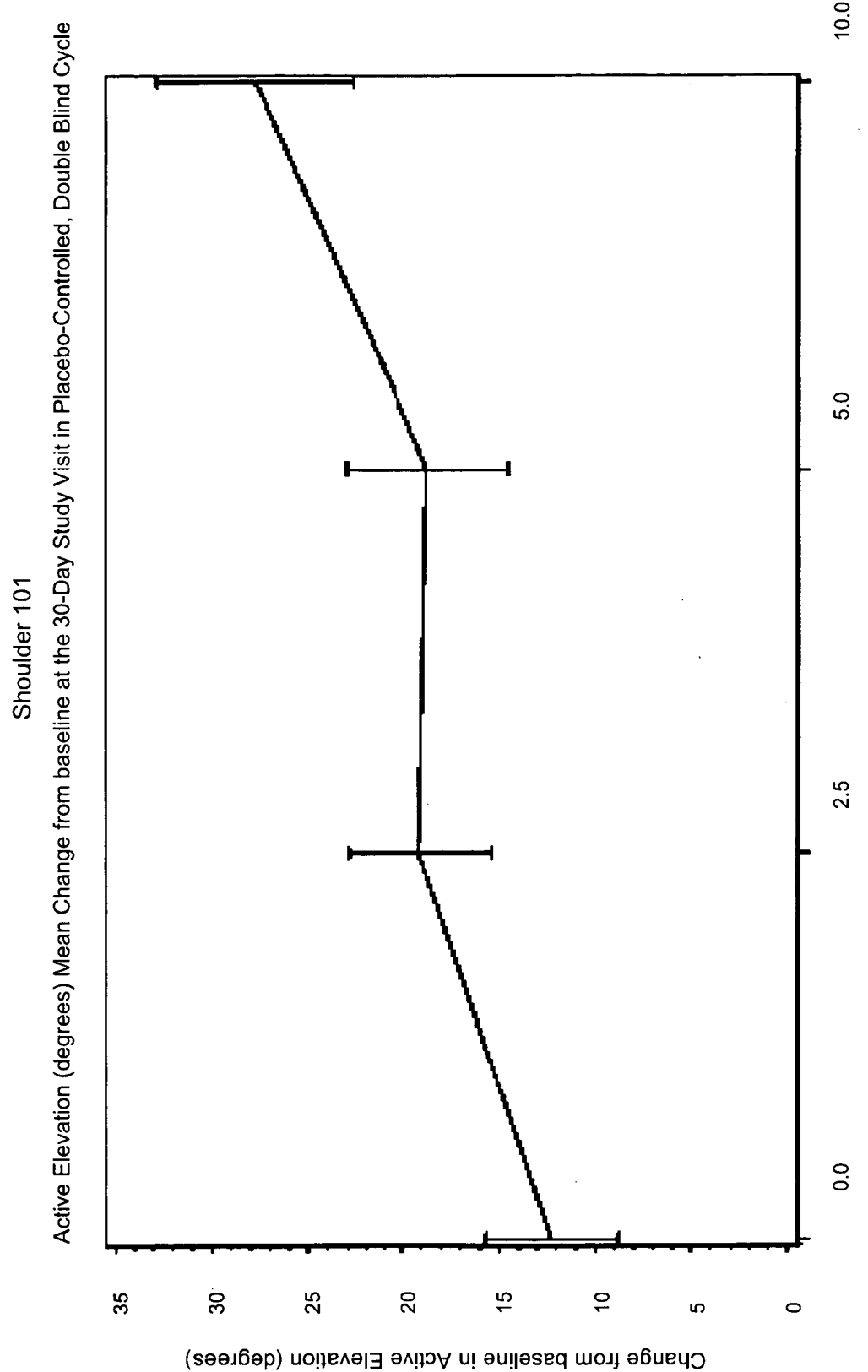

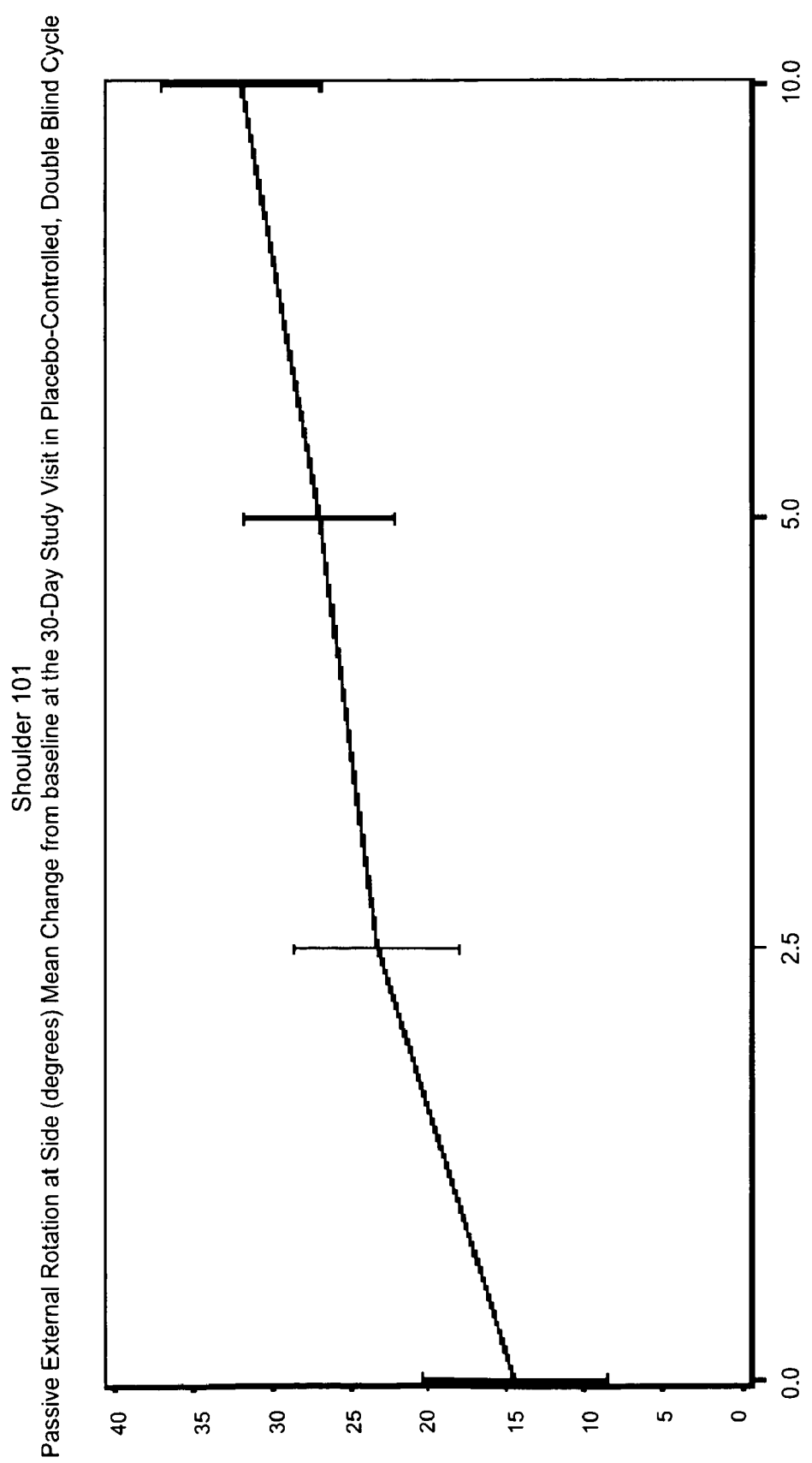

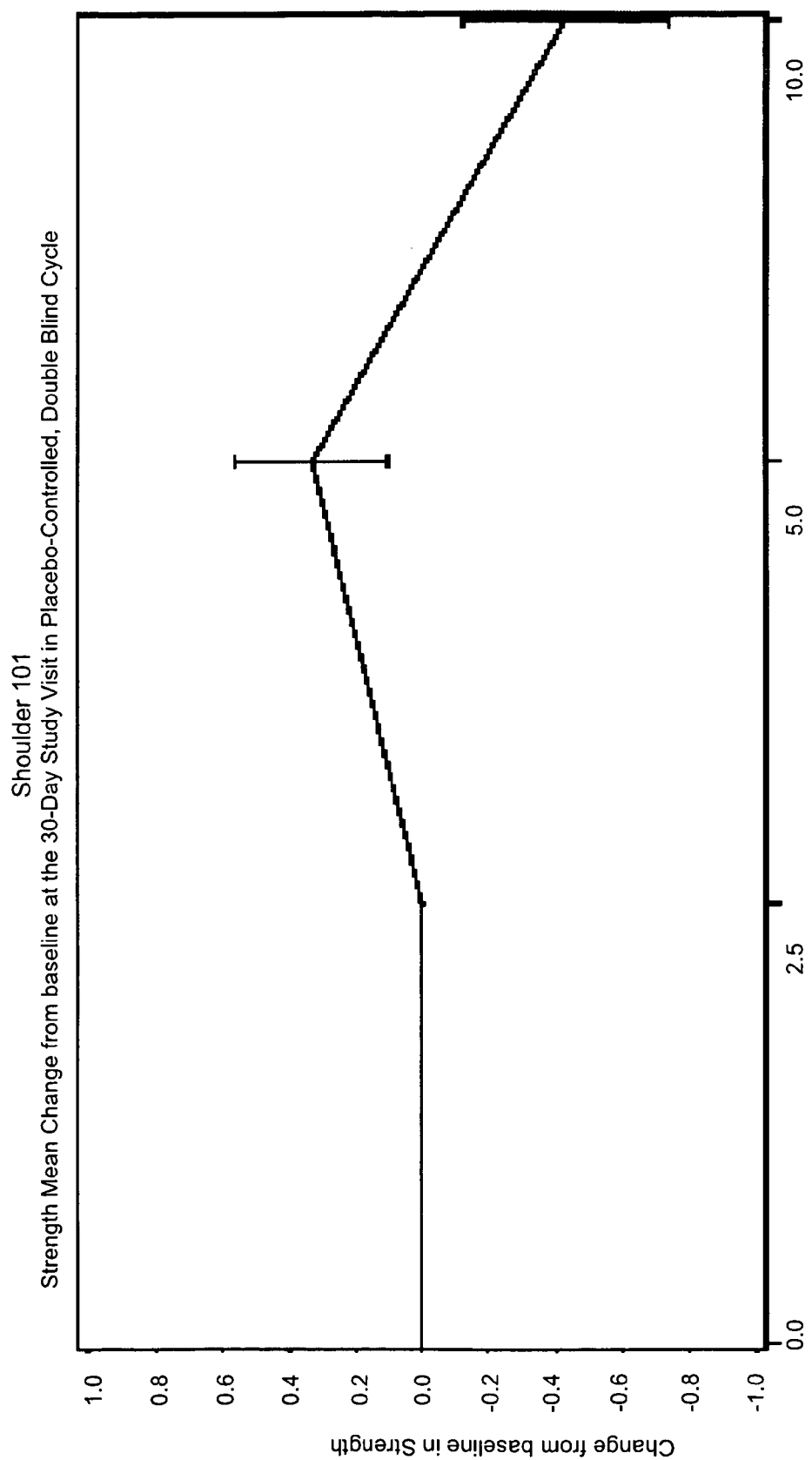

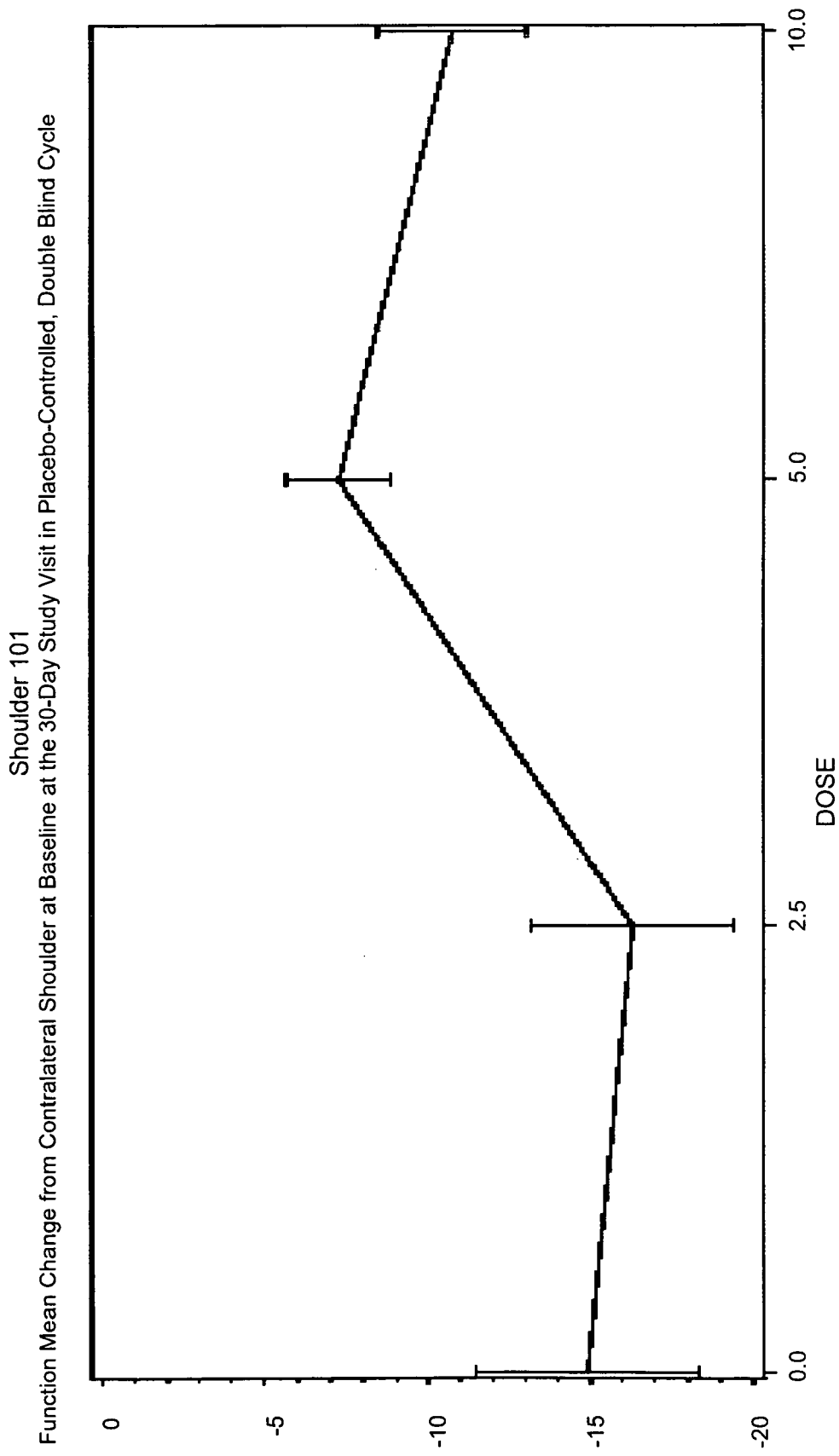

METHODS FOR TREATING ADHESIVE CAPSULITIS

RELATED APPLICATIONS

This application is a continuation of Ser. No. 11/335,157, filed Jan. 19, 2006, which claims the benefit of U.S. Provisional Application No. 60/645,772, filed on Jan. 21, 2005, U.S. Provisional Application No. 60/677,440, filed on May 3, 2005 and U.S. Provisional Application No. 60/719,470, filed on Sep. 22, 2005. The entire teachings of the above applications are incorporated herein by reference.

GOVERNMENT SUPPORT

The invention was supported, in whole or in part, by a grant RR10710 from the National Institutes of Health. The Government has certain rights in the invention.

BACKGROUND OF THE INVENTION

Adhesive capsulitis (frozen shoulder) is a clinical syndrome of severe pain and significantly decreased shoulder motion which may occur idiopathically, after trauma or affect patients with diabetes and/or thyroid disorders. The duration of the disorder may be from months to years and severely affect the quality of life. Lengthy physical therapy, sometimes including cortisone injections and/or manipulation under anesthesia and/or shoulder arthroscopy, currently are the standards of orthopedic care. However, more effective therapies are needed.

SUMMARY OF THE INVENTION

The invention relates to the discovery that collagenase injections are effective in lyse the collagenous adhesions in the shoulder capsule and treat the disorder, adhesive capsulitis. As such, the invention relates to methods of treating or preventing adhesive capsulitis, or frozen shoulder, in a subject in need of such treatment comprising injecting or otherwise delivering an effective amount of collagenase to the collagenous adhesions in the shoulder. The invention also relates to the use of collagenase in the manufacture of a medicament to treat adhesive capsulitis.

DETAILED DESCRIPTION OF THE INVENTION

Figure 1:
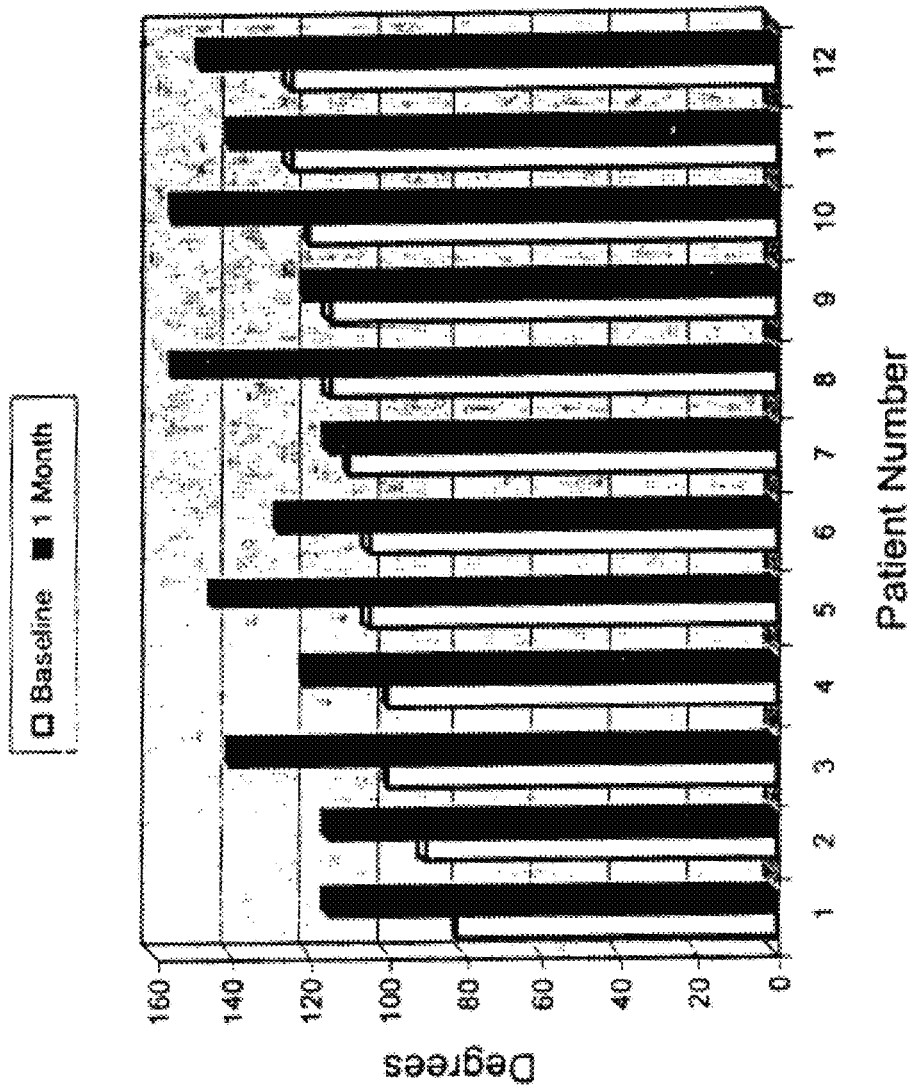
FIG. 1 is a bar graph that reports the improved mobility, or active elevation, in twelve patients who received a third collagenase injection.

The invention relates to the discovery that collagenase injections are effective in lyse the collagenous adhesions in the shoulder capsule and treat the disorder, adhesive capsulitis. As such, the invention relates to methods of treating or preventing adhesive capsulitis, or frozen shoulder, in a subject in need of such treatment comprising injecting or otherwise delivering an effective amount of collagenase to the collagenous adhesions in the shoulder capsule. The invention also relates to the use of collagenase in the manufacture of a medicament to treat adhesive capsulitis.

Collagenase injections have been proposed for the treatment of diseases such as Duptyren's disease and Peyronie's disease. Both diseases are associated with collagen plaques or cords. Wegman, Thomas L., U.S. Pat. No. 5,589,171, Dec. 31, 1996, U.S. Pat. No. 6,086,872, Jul. 11, 2000 and U.S. Pat. No. 6,022,539, Feb. 8, 2000, which are incorporated herein by reference.

Collagenase is an enzyme that has the specific ability to digest collagen. A preferred form of collagenase is derived from fermentation by Clostridium histolyticum, and is purified by a chromatographic technique.

Sterilized lyophilized collagenase powder is commercially available having a minimum assay of 50 ABC units per mg. The assay may range considerably above that from batch to batch, but is taken into account in determining the weight of powder to use with a pharmaceutically acceptable carrier, e.g. normal saline, in preparing a desired concentration for treatment.

A preferred collagenase composition comprising a mixture of collagenase I and collagenase II in a mass ratio of about 1 to 1 and having specific activity of at least about 700 SRC units/mg, such as at least about 1000 SRC units/mg, more preferably at least about 1500 SRC units/mg. One SRC unit will solubilize rat tail collagen into ninhydrin reaction material equivalent to 1 nanomole of leucine per minute, at 25° C., pH 7.4. Collagenase has been described in ABC units as well. This potency assay of collagenase is based on the digestion of undenatured collagen (from bovine tendon) at pH 7.2 and 37 degrees C. for 20-24 hours. The number of peptide bonds cleaved are measured by reaction with ninhydrin. Amino groups released by a trypsin digestion control are subtracted. One net ABC unit of collagenase will solubilize ninhydrin reactive material equivalent to 1.09 nanomoles of leucine per minute. 1 SRC unit equal approximate 6.3 ABC unit or 18.5 GPA unit.

The collagenase is preferably administered via injection in a liquid carrier that is pharmaceutically acceptable. Preferably the carrier does not interact or deactivate the collagenase. Examples are normal saline, aqueous NaCl/CaCl2 buffer (e.g., containing 0.9% NaCl and 2 mM $CaCl_2$), aqueous dextran solution, and aqueous hetastarch solution. For example, the lyophilized formulation can contain 0.1 mg lactose monohydrate per 1,000 ABC units. Each glass vial used below contained 5,150 ABC units of enzyme.

In accordance with the invention, collagenase in a liquid carrier is injected into a collagen adhesion within the shoulder capsule. The amount and concentration of collagenase used are effective to soften and relax or rupture the adhesion.

The total volume of liquid injected preferably does not exceed about 0.50 ml. A smaller volume down to about 0.25 ml to about 0.1 ml is usually more preferred.

Preferably, the injection is a sterile one given between the interval of the deltoid and pectoral muscles. An anesthesia injection of 5-10 ml sterile 1% lidocaine preferably precedes the collagenase injection for the comfort of the patient.

The total dosage is preferably injected in one portion, although two or more portions at the same or different points into the shoulder capsule are possible, preferably intralesionally, or intra-adhesionally. The objective of these procedures is to assure good distribution of the collagenase within a small volume of the adhesion. Preferably, the patient wears a sling to immobilize the shoulder for approximately 5-6 hours post injection. Patients perform at home physical therapy for at least one month to assist in the return of normal range of shoulder motion.

In other embodiments, the collagenase can be administered locally and topically (e.g., via a transdermal patch or topical cream or ointment), preferably at site proximal to the affected shoulder or can be administered via an implant (e.g., microcapsules or microspheres which release the collagenase over time).

The subject can be any animal, preferably a mammal or human patient. Examples of animals that can be treated according to the invention include domestic animals (such as cats, dogs, etc.), farm animals (such as horses, cows, pigs, etc.) and exotic animals (such as monkeys, apes, etc.). Preferred human patients are those that have decreased shoulder motion which occurred idiopathically, after trauma or patients with diabetes and/or thyroid disorders.

In one embodiment, the patient is characterized as having extremely decreased shoulder motion in all planes to include active elevation, active internal rotations (spine level reached by the thumb behind the back), active external rotation, passive elevation, passive external rotation at the side, passive external rotation at 90 degrees, function scores. Pain is increased to a level where it interferes with activities of daily living and diminishes the quality of life. The invention can achieve improvement in all planes of motion of the shoulder or decreased pain or alleviation of another symptom of the disorder.

In cases where results of a single treatment are considered inadequate, the same procedures, total amount of collagenase and concentration may be repeated. Successful clinical results were achieved with repeated injections at 4 to 6 week intervals.

EXPERIMENTAL

Example 1

Methods

Forty patients entered the study protocol, 11 males and 29 females, mean age 52±8.9 years. At the time of initial presentation, the mean length of time that all patients had adhesive capsulitis was 16 months (range 2-144 mo). Eighteen patients were idiopathic, six patients were Type 1 and six patients were Type 2 diabetics, five patients had hypothyroidism, three patients had hypothyroidism and diabetes, and two patients were affected by post-traumatic adhesive capsulitis. Following a 10 ml 2% lidocaine injection for local anesthesia, all patients received a first, random placebo controlled double blind injection of either 0.145 mg, 0.29 mg or 0.58 mg Clostridial collagenase or placebo (0.9% saline containing 2 mM calcium) directed at the anterior capsule, 0.5 ml total volume. Patients were evaluated serially for one month based on the American Society of Shoulder and Elbow Surgeons Shoulder Evaluation form which scores pain, shoulder motion, strength, stability and function. Shoulder motion evaluations were measured in degrees and consisted of: active/passive elevation, active/passive external rotation, passive external rotation at 90 degrees and active internal rotation (spine level reached by thumb posteriorly). If the shoulder motion scores or pain scores were not statistically significant from baseline values, patients had the option of proceeding to additional open label 0.58 mg collagenase injection(s) administered at 4-6 week intervals. Nine patients received only one (random placebo double blind) injection, 30 patients received a second open label 0.58 mg collagenase injection. The control treatment code for the first random placebo double blind injection (dose response) may not be unmasked until the total of 60 patients has been enrolled. However, the results of the open label collagenase injections have shown clear and significant merit. All patients were followed, using the shoulder evaluation form, at two, three, six, nine, 12 and 24 months post their last injection. Mean length of follow-up was 10.8±8.2 months. Statistical analysis consisted of testing the mean change from baseline shoulder evaluations by the student's t test.

Results

Thirty of the 40 patients required a short series of repeat open label 0.58 mg collagenase injections after a first random, placebo, double blind injection. Table 1 shows the mean increases in should range of motion, function and pain in the affected shoulders comparing baseline parameters to the one month post $2^{nd}$ and $3^{rd}$ injection follow-ups. All increases were statistically significant, $p<0.0001$. Diabetic patients (n=15) showed smaller increases from baselines in active and passive external rotation, internal rotation (spine level) and passive elevation when compared to idiopathic patients (n-18). For example, for active external rotation at one month post the second injection, the mean increase in idiopathic patients was $31.4°±14.1°$ but only $20.5°±15.5°$ in diabetic patients ($p=0.02$). Patients with hypothyroidism and post-trauma patients showed equal rates of recovery of shoulder motion compared to idiopathic patients. Improvements in should motion, pain and function were sustained in the longer term, mean length of follow up 10.8±8.2 months.

Adverse effects of injections included tenderness at the injection site in all patients and biceps ecchymosis in approximately two-thirds of patients. These resolved without even in 7-14 days.

TABLE 1

Treated shoulder and contralateral shoulder at baseline

|  | $2^{nd}$ Injection (n = 30) | $3^{rd}$ Injection (n = 12) |
|---|---|---|
| Active elevation | 30.8° ± 15.7° | 36.8° ± 13.5° |
| Passive elevation | 25.4° ± 16.5° | 25.8° ± 17.5° |
| Active external rotation | 27.4° ± 15.4° | 39.0° ± 16.3° |
| Passive external rotation | 37.2° ± 22.0° | 40.3° ± 22.2° |
| Passive external rotation at 90° | 21.8° ± 18.9° | 27.8° ± 15.6° |
| Internal rotation (spine level) | +5 levels ± 3.8 levels | +6 levels ± 4.8 levels |
| Function | +20 points ± 8 points | +23.5 points ± 11 points |
| Pain | 4 (slight) | 4 (slight) |

Conclusions

After a first random, placebo, double blind injection, the majority of patients (30 of 40) required a short series of open label (0.58 mg) collagenase injections before significant improvements were seen in shoulder motion, pain and function. Therefore, despite the fact that the first injection treatment code for dose response is still masked to the investigators, it is clear that collagenase injection of adhesive capsulitis has shown significant merit. Open label collagenase treatment resulted in significantly reduced time in return to pain free function when compared to the standard Orthopaedic care, which can last for many months or even years. This Phase 2 study has shown that collagenase injection of the shoulder capsule is a safe and effective method of treatment for adhesive capsulitis, which warrants continued investigation within the FDA regulatory process.

Example 2

The purpose of this FDA regulated, prospective, Phase II, random, placebo controlled, double blind, dose response study was to develop a nonoperative method for treatment of adhesive capsulitis (frozen shoulder) using collagenase injection therapy.

Sixty patients entered the study protocol, 47 females and 13 males, mean age 52 years, mean duration of adhesive capsulitis, 17 months. All patients received a first, random, placebo controlled, double blind, extra-articular injection of either physiologic saline (n=15), or 0.145 mg (n=16), or 0.29 mg (n=15), or 0.58 mg (n=14) collagenase, 0.5 ml total volume, directed at the anterior shoulder capsule. Patients were serially evaluated for 1 month for shoulder range of motion in all planes, pain, and function. At 1 month, if motion, pain and functional scores were not significantly different from baseline, patients had the option of receiving up to four additional 0.58 mg collagenase injections, given six weeks apart.

In the open-label portion of the study, for the first open-label course, n=13, 12, 9, and 10 for, respectively, placebo, 2,500 unit, 5,000 unit, and 10,000 unit treatment groups, except for active elevation and passive elevation for which n=9 for the 5,000 unit group. For the second open label course, n=7, 7, 4, and 6 for, respectively, placebo, 2,500 unit, 5000 unit, and 10,000 unit treatment groups. For subjects with the contralateral shoulder measured at baseline, in the first open label course, n=10, 8, 8, and 8 for, respectively, placebo, 2,500 unit, 5000 unit, and 10,000 unit treatment groups. For the second open label course, n=4, 5, 3, and 5 for, respectively, placebo, 2,500 unit, 5000 unit, and 10,000 unit treatment groups for subjects with contralateral shoulder measurements at baseline. Three subjects in the data received had data for a third.

Results of the random placebo controlled, dose response study showed that there were statistically significant differences in drug treatment vs. placebo in restoration of normal shoulder motion and function, with minimal pain and the 0.58 mg dose trending to be the most efficacious. A majority of patients required second (n=19) and third (n=19), open label 0.58 mg collagenase injections and continued to show significant improvements in motion, function and pain. This study has shown that a short series of collagenase injections of the shoulder capsule for adhesive capsulitis is a safe and effective method of treatment which warrants continued investigation within the FDA regulatory process.

Sixty subjects completed the nominal day 30 visit in the double-blind phase and provided data for statistical analysis. The sample sizes for placebo, 2500 units, 5,000 units, and 10,000 units treatments were, respectively, 15, 16, 15, and 14. Of those 60 subjects, 46 had data for the contralateral shoulder at baseline: 12, 10, 12, and 12 subjects for, respectively, the placebo, 2,500 units, 5,000 units, and 10,000 units treatment groups.

TABLE 1

Treated shoulder and contralateral shoulder at baseline

| | Contralateral shoulder (n = 46) | Treated shoulder (n = 60) |
|---|---|---|
| Active elevation (degrees) | 166.9 ± 12.4 | 112.1 ± 19.6 |
| Active external rotation (degrees) | 77.1 ± 14.0 | 26.6 ± 16.7 |
| Active internal rotation (spine level) | 14.4 ± 3.6 | 5.3 ± 2.34 |
| Passive elevation (degrees) | 175.3 ± 8.1 | 130.4 ± 17.2 |
| Passive external rotation (degrees) | 86.1 ± 10.0 | 28.0 ± 18.0 |
| Passive external elevation @ 90° (degrees) | 103.8 ± 11.1 | 69.4 ± 15.3 |
| Function score (0-60 scale) | 60.0 ± 0 | 32.0 ± 7.6 |
| Pain score (0-5 scale) | 5.0 ± 0 | 2.0 ± 0.9 |

For the protocol-defined success criteria, none of the outcome measures approached statistical significance for any active treatment compared to placebo. One might wonder if the protocol-defined success criteria, drawn from published standards, are too strict for the population in this study. Comparison of the contralateral shoulder means to the published standards seems to not support that. For example, the protocol-defined criteria for active elevation and active internal rotation (spine level) are 160 degrees and 10 degrees, respectively, but, from Table 1, the subjects in this study had better functionality at baseline in the contralateral shoulder for these two outcome measures than the published standards stipulate.

TABLE 2

Means at the 30-day double-blind visit adjusted for baseline of treated shoulder

| | Placebo (n = 15) | 2,500 u (n = 16) | 5,000 u (n = 15) | 10,000 u (n = 14) |
|---|---|---|---|---|
| Active elevation (degrees) | 124.5 | 131.9 | 130.2 | 139.7 |
| Active external rotation (degrees) | 42.4 | 42.3 | 52.6* | 48.6 |
| Active internal rotation (spine level) | 8.0 | 8.4 | 8.4 | 7.9 |
| Passive elevation (degrees) | 145.5 | 145.2 | 148.6 | 145.9 |
| Passive external rotation (degrees) | 44.5 | 49.3 | 55.6 | 59.5 |
| Passive external elevation @ 90° (degrees) | 83.8 | 81.7 | 89.4 | 87.9 |
| Function score (0-60 scale) | 43.0 | 44.2 | 48.6 | 49.8 |
| Pain score (0-5 scale) | 3.3 | 3.4 | 3.9 | 3.4 |

*p ≦ 0.05

The analysis of covariance adjusted the double-blind phase treatment means for their different baseline values so that, in effect, each treatment had the same mean for the treated shoulder at baseline. With that adjustment, four of the eight outcome measures analyzed showed activity for the 5,000 unit or 10,000 unit treatments (Table 2). The 10,000 unit dose showed activity, relative to placebo, for active elevation, passive elevation, and function score. The 5,000 unit treatment showed activity for active external rotation. It is worth noting that for each of those four outcome measures, subjects in the placebo group had, on average, less favorable or just about less favorable, outcomes than any group receiving active treatment.

The exploratory analyses of the open-label data supported results of the analysis of covariance of the double-blind data.

After one open-label course, subjects had received a total of 10,000 units, 12,500 units, 15,000 units, or 20,000 units of collagenase, depending on their treatment group in the double-blind phase. For active elevation, the change from the treated shoulder baseline or the contralateral shoulder baseline is consistent with an active collagenase treatment. For example, relative to the treated shoulder baseline, active elevation improved by 43.6 degrees for the 10,000 unit group but only 28.3 degrees for the placebo group. For function score, the improvement for the 10,000 unit group was 21.6 points on the 60-point scale versus an improvement of 20.6 points for the placebo group. Some outcome measures did show more improvement for the placebo group than for the collagenase treated groups. For example, for active external rotation, the group that received placebo in the double-blind phase (n=15) had a change from baseline of 35.2 degrees after one course of open-label treatment (n=13 subjects continued from the double-blind phase) but the group that received 10,000 units in the double-blind phase (n=14) had a change from baseline after an additional 10,000 units of only 27 degrees (n=10 continued from the double-blind phase).

Discussion

The study set out to demonstrate that a single collagenase injection of 2,500, 5,000, or 10,000 units is more efficacious than placebo injection for adhesive capsulitis. The protocol stipulates dichotomous "success" criteria for 11 outcome measures and those clearly were not met. The protocol also stipulates a more sensitive analysis of the data using the analysis of covariance and that approach does provide evidence that collagenase had activity in this study.

Eight of the outcome measures were analyzed with the analysis of covariance and four of the eight did present evidence of collagenase activity. Active elevation, passive elevation, and function score had p-values<0.05 for the comparison of placebo to the 10,000 unit treatment. For active external rotation, the 5,000 unit treatment had a p-value<0.05, although the 10,000 unit dose did not. For passive external elevation at 90°, placebo has an adjusted mean of 83.8 degrees versus an adjusted mean of 87.9 for the 10,000 unit treatment although the p-value for this difference is not less than 0.05. The remaining three outcome measures: active internal rotation (spine level), passive elevation, and pain score were not at all sensitive to any collagenase effect, with placebo and collagenase very similar.

The gold standard in clinical trials is protocol-specified analysis of data collected in a randomized, placebo-controlled, double-blind study and with that gold standard, as discussed above, there is evidence that collagenase has activity in adhesive capsulitis.

Aside from evidence collected with the gold standard, supportive or exploratory analysis can provide important corroboration. The open-label portion of this study, particularly for active elevation and function score, does corroborate the double-blind portion. The open label portion of the study suggests that additional injections may be of benefit.

Conclusion

The outcome measures of active elevation, active external rotation, passive elevation, and function score, as analyzed in the analysis of covariance of the double-blind data, do show evidence of activity in adhesive cap sulitis of the shoulder. The three collagenase doses administered in this study did not meet the protocol-defined criteria for "success" therefore it cannot be concluded that a single injection of collagenase, even at the highest dose of 10,000 units, is efficacious.

Example 3

Figure 2:
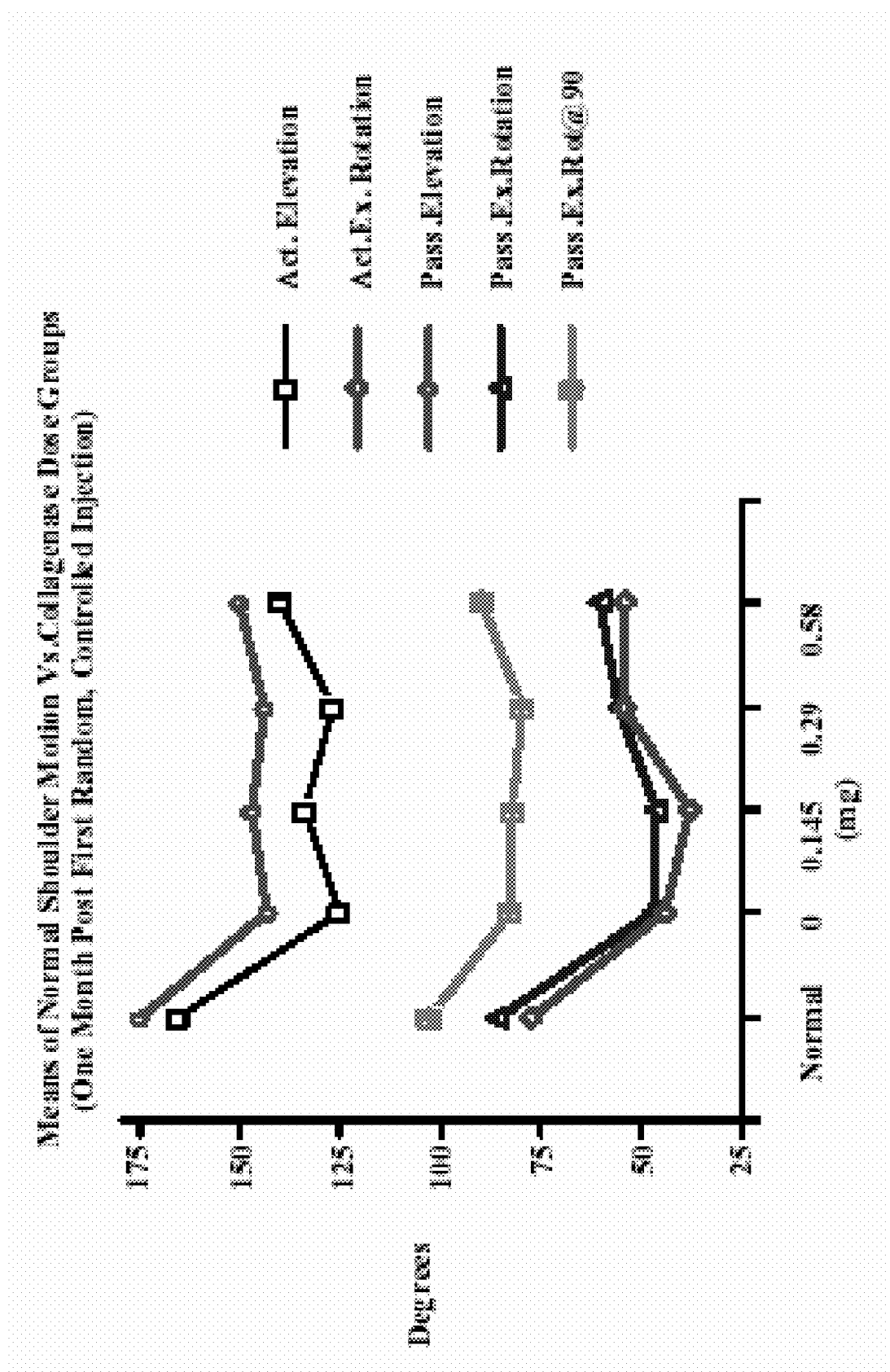
FIG. 2 is a line graph of the means of normal shoulder motion vs. collagenase dose groups.

At one month after the first random, placebo controlled, double blind injection in all 60 patients, shoulder motion was improved, but not to normal values. The highest collagenase dose (0.58 mg) trended as the most effective (FIG. 2). Function scores were 70% of normal for placebo, 73% for 0.145 mg collagenase, 81% for 0.29 mg and 83% for 0.58 mg. Pain scores were 66% of normal for placebo and the 0.145 mg dose and 74% of normal for both the 0.29 mg and 0.58 mg doses. The spine levels reached behind the back (active internal rotation) were L3 for placebo and L2 for all collagenase doses. Normal spine level was T8. Fourteen patients required only the first injection because they responded to normal after one month.

Figure 3:
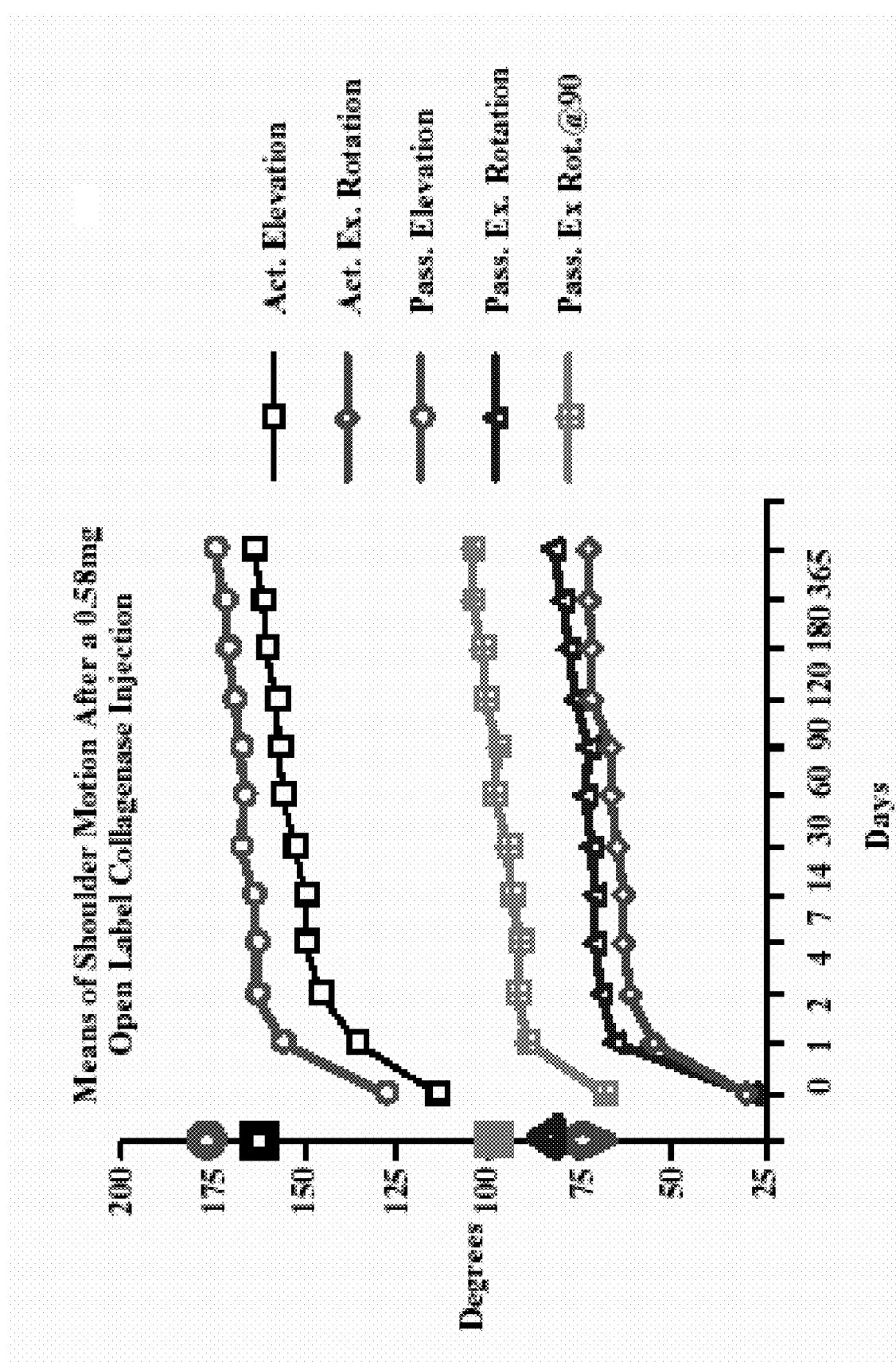
FIG. 3 is a line graph of the means of shoulder motion after a 0.58 open label collagenase injection.
Figure 4B:
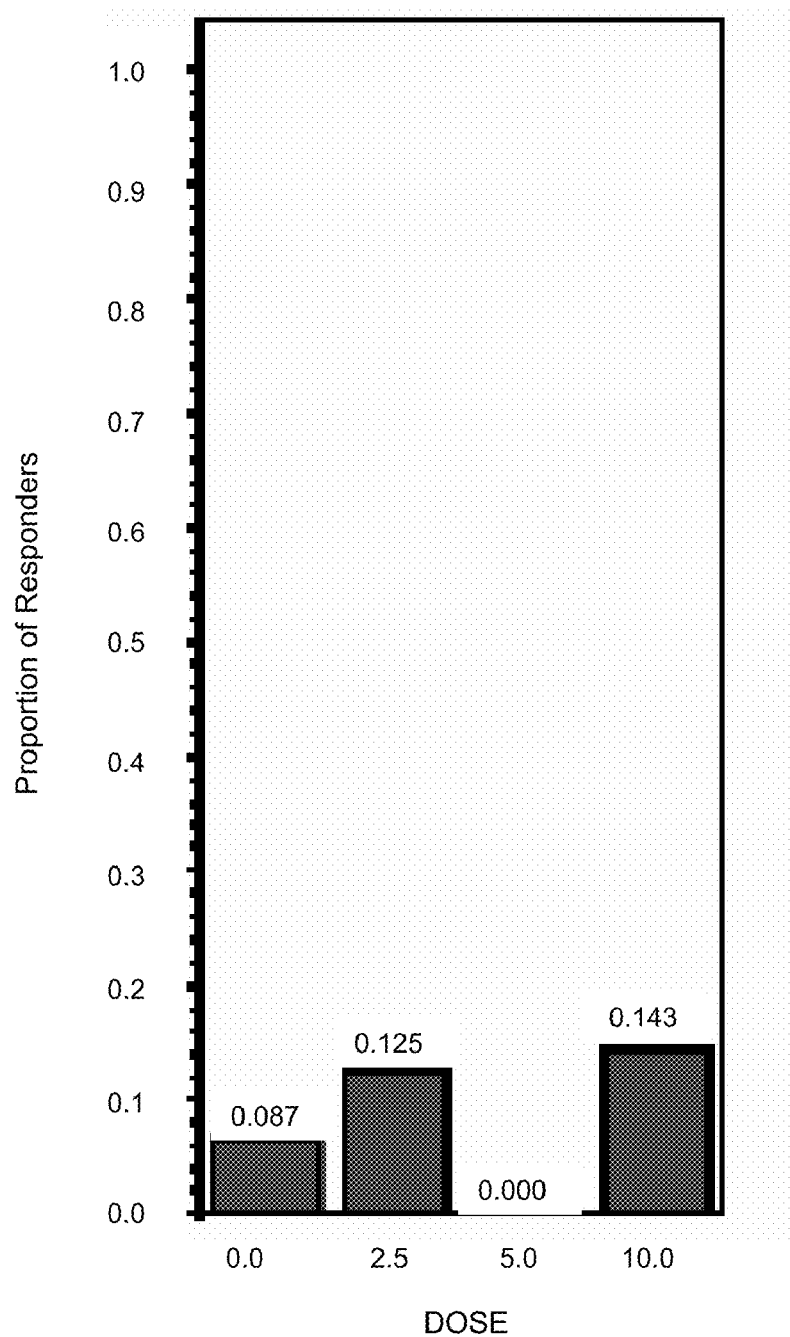
FIGS. 4A-4EE are line and bar graphs depicting the data obtained in the clinical trial described herein.
Figure 4C:
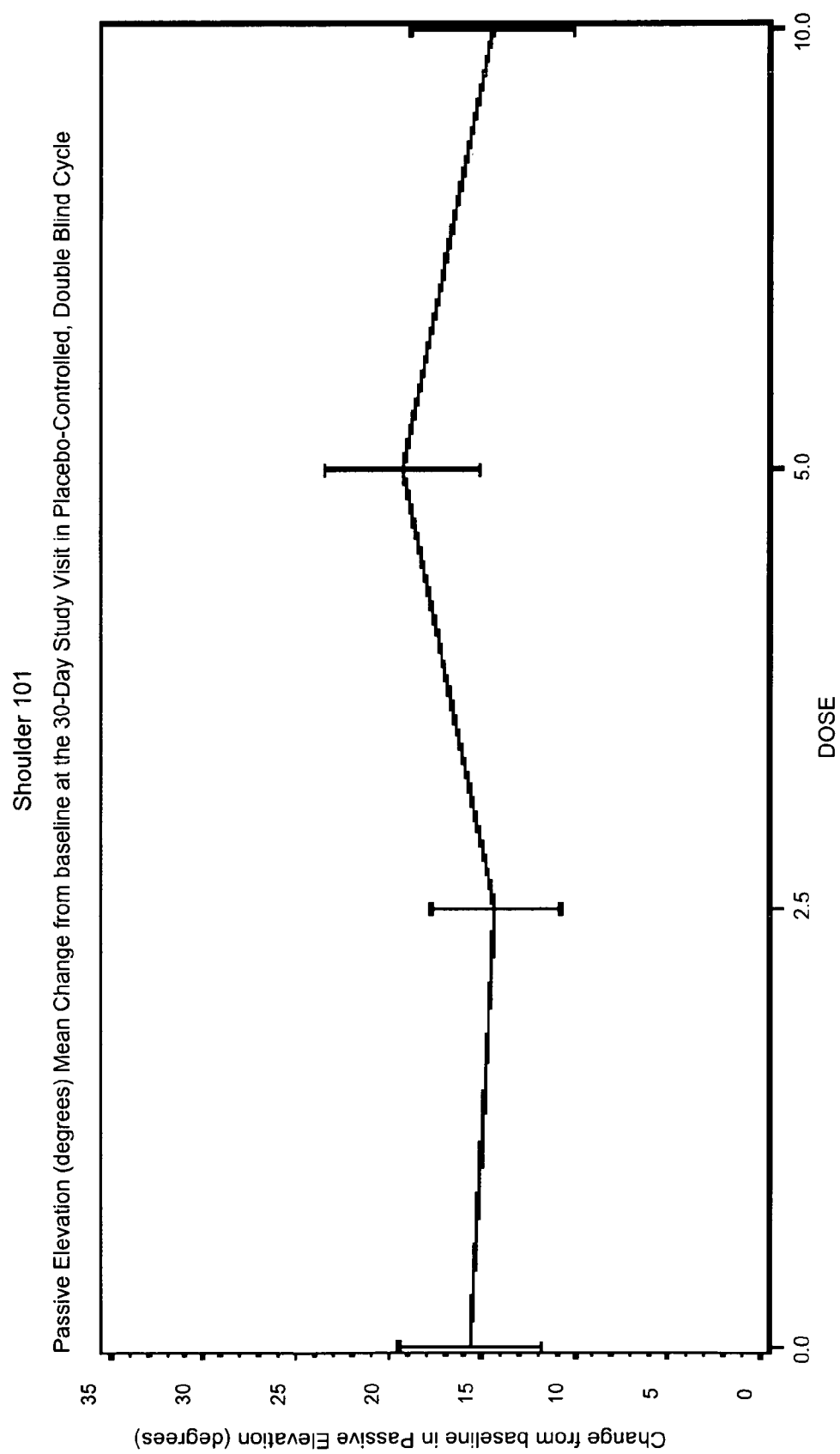
Figure 4D:
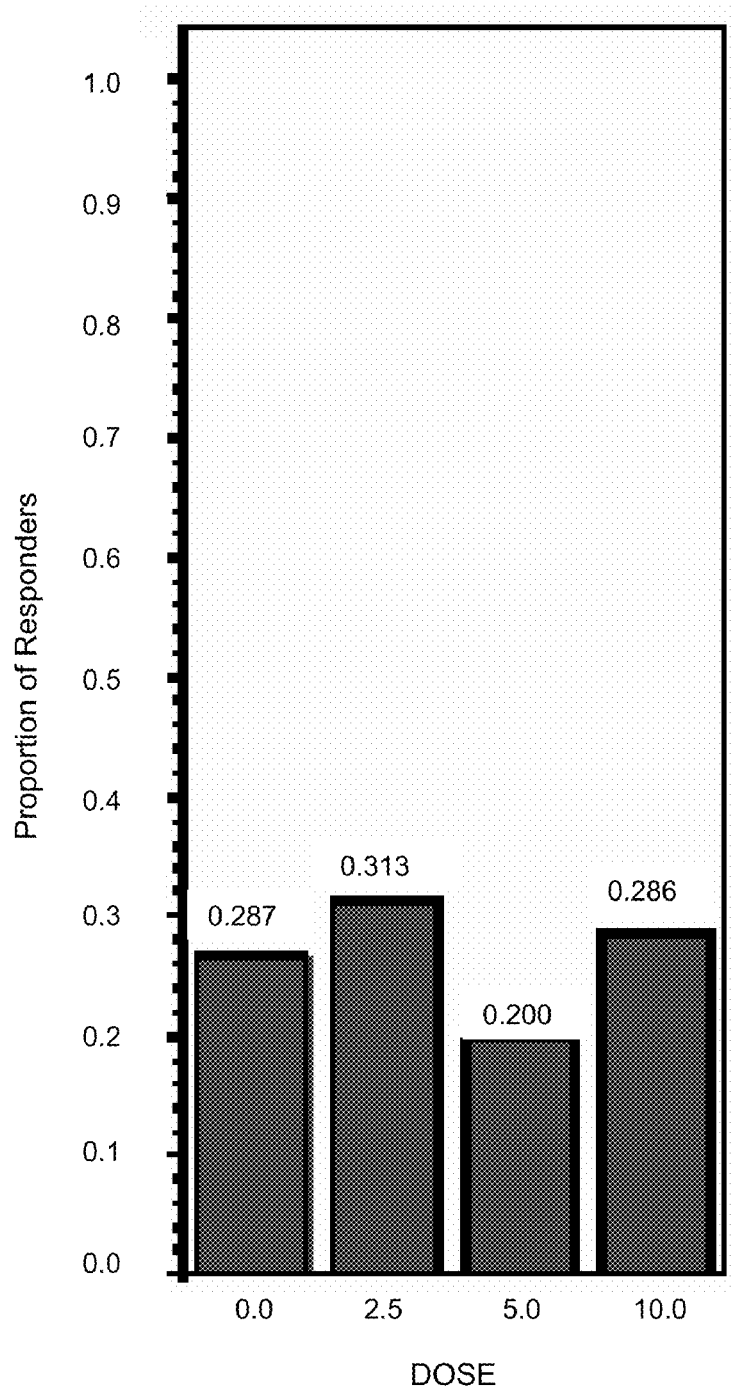
Figure 4E:
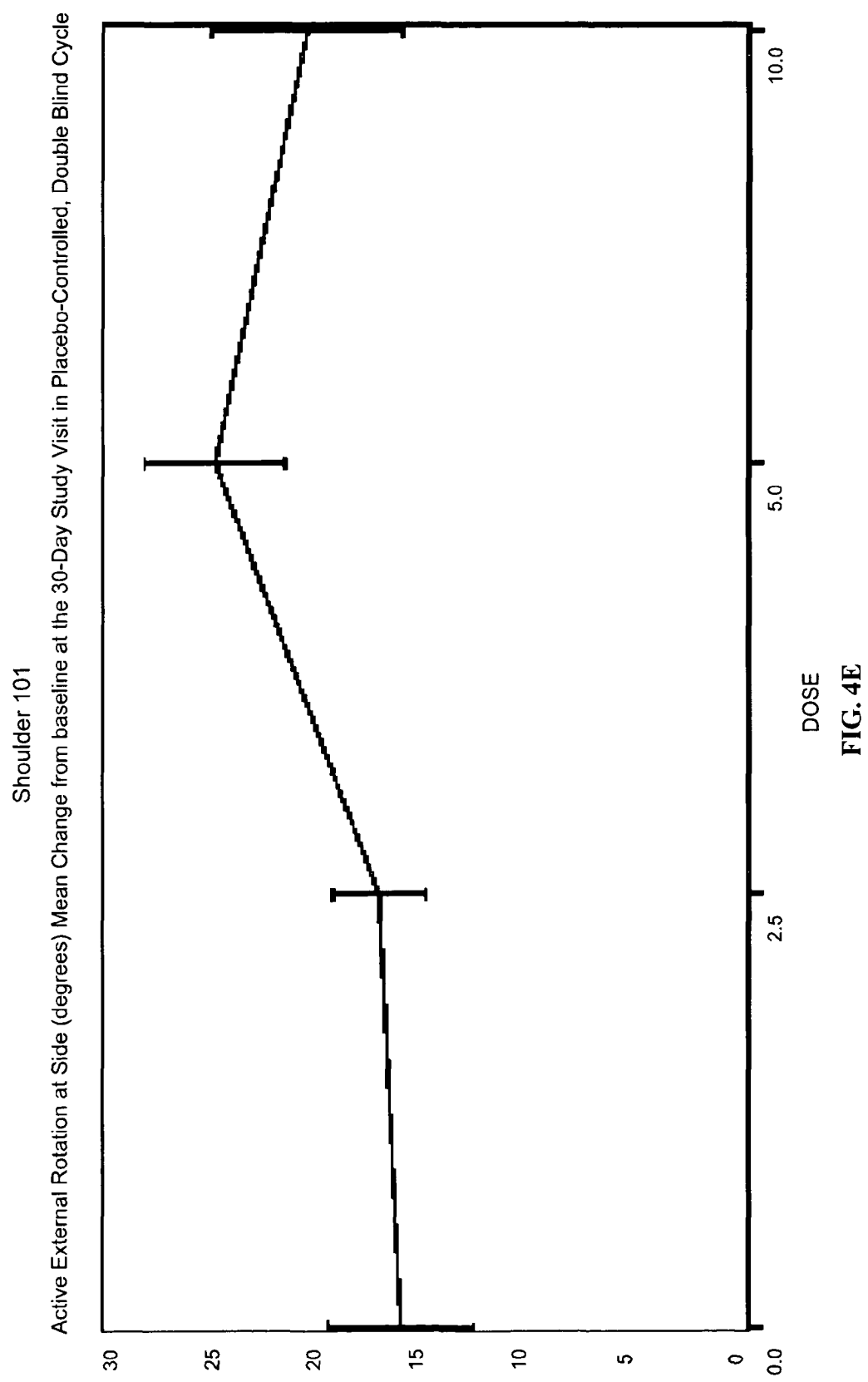
Figure 4F:
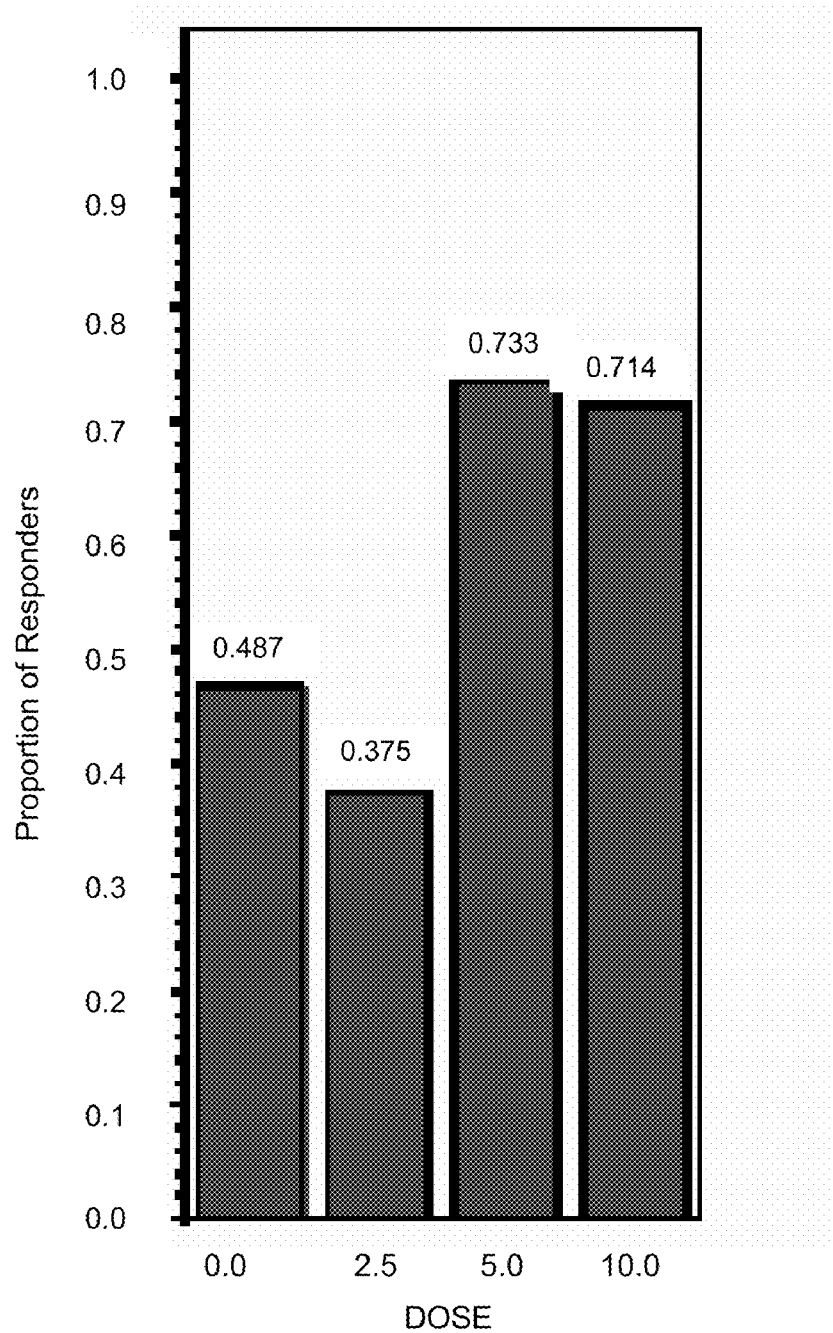
Figure 4H:
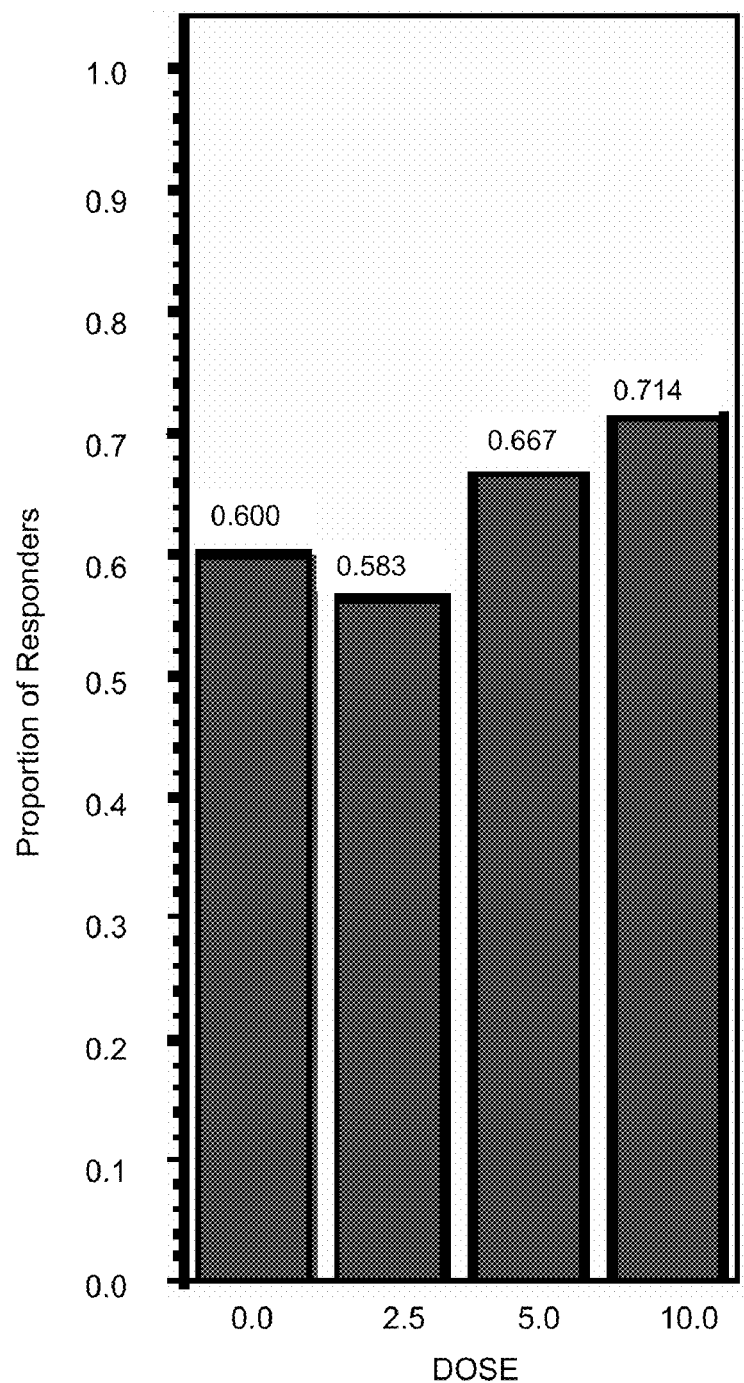
Figure 4I:
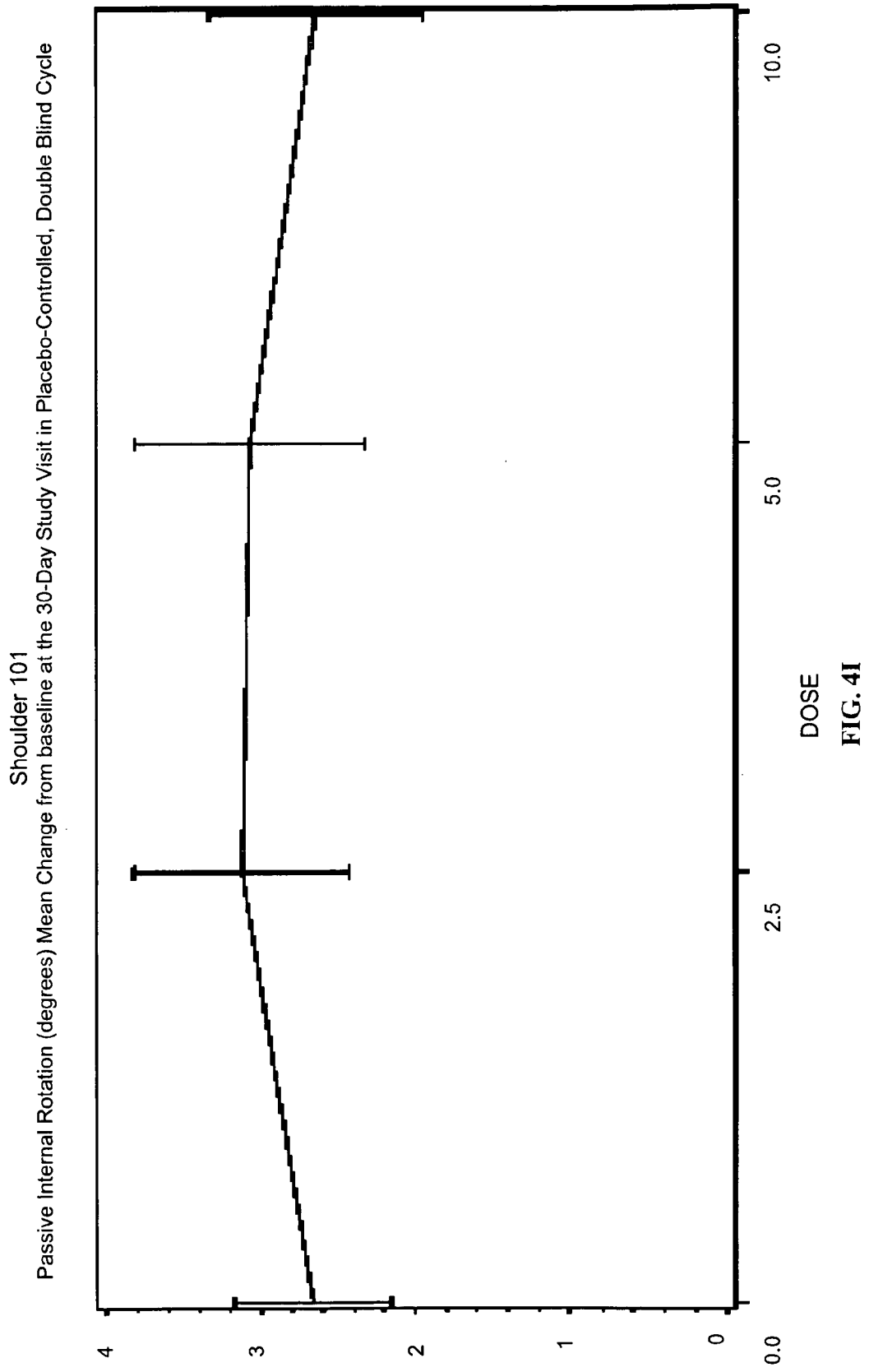
Figure 4J:
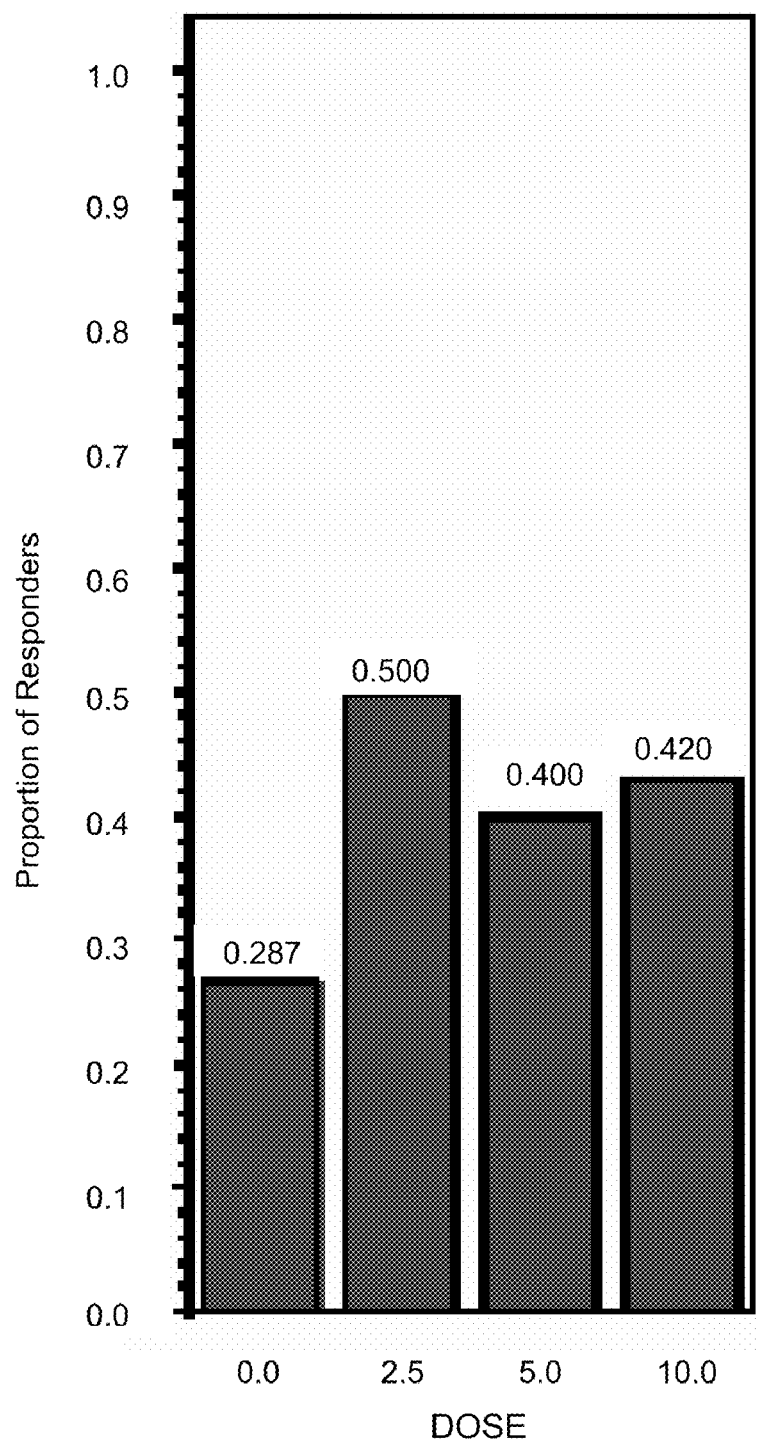
Figure 4K:
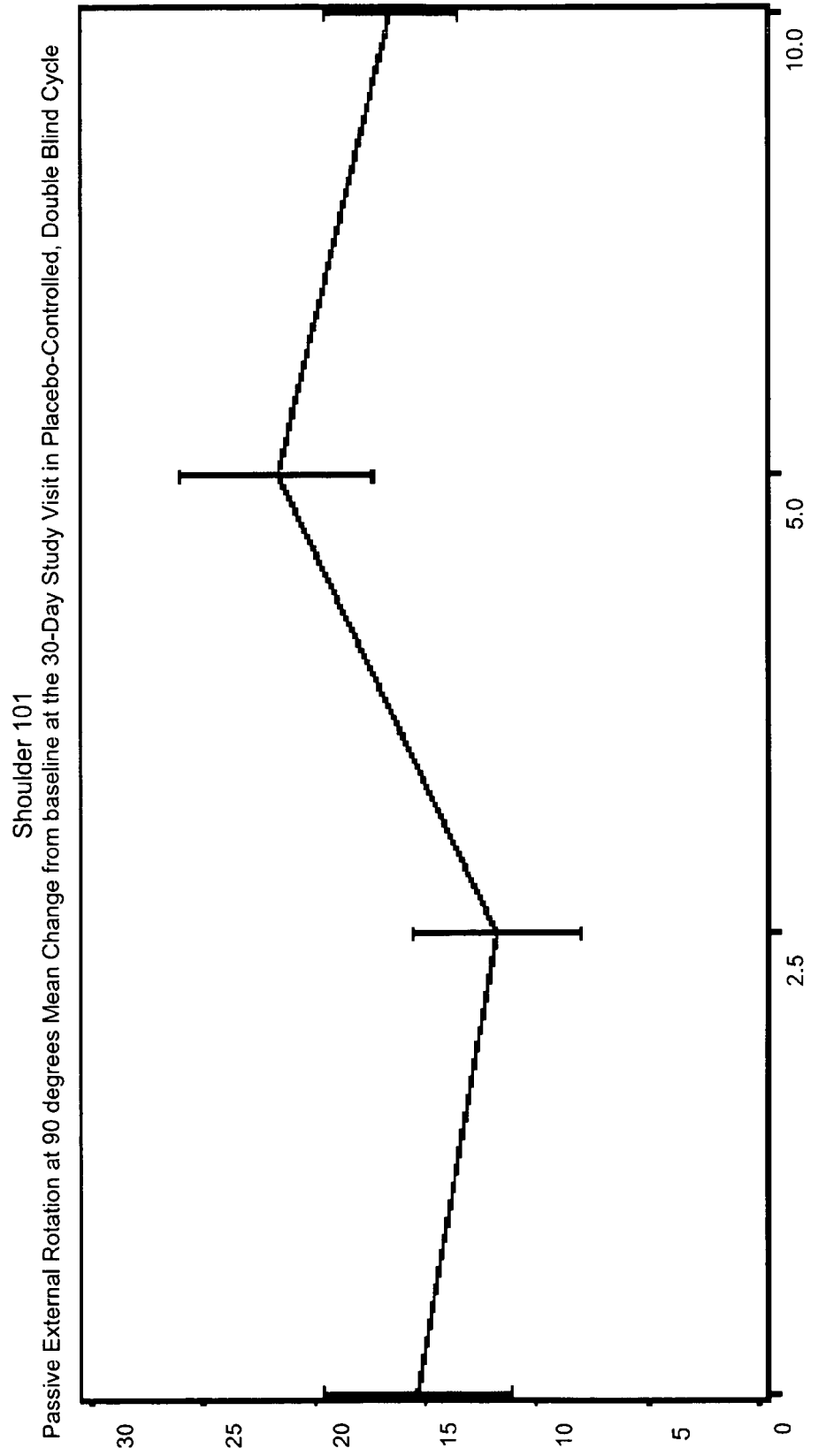
Figure 4L:
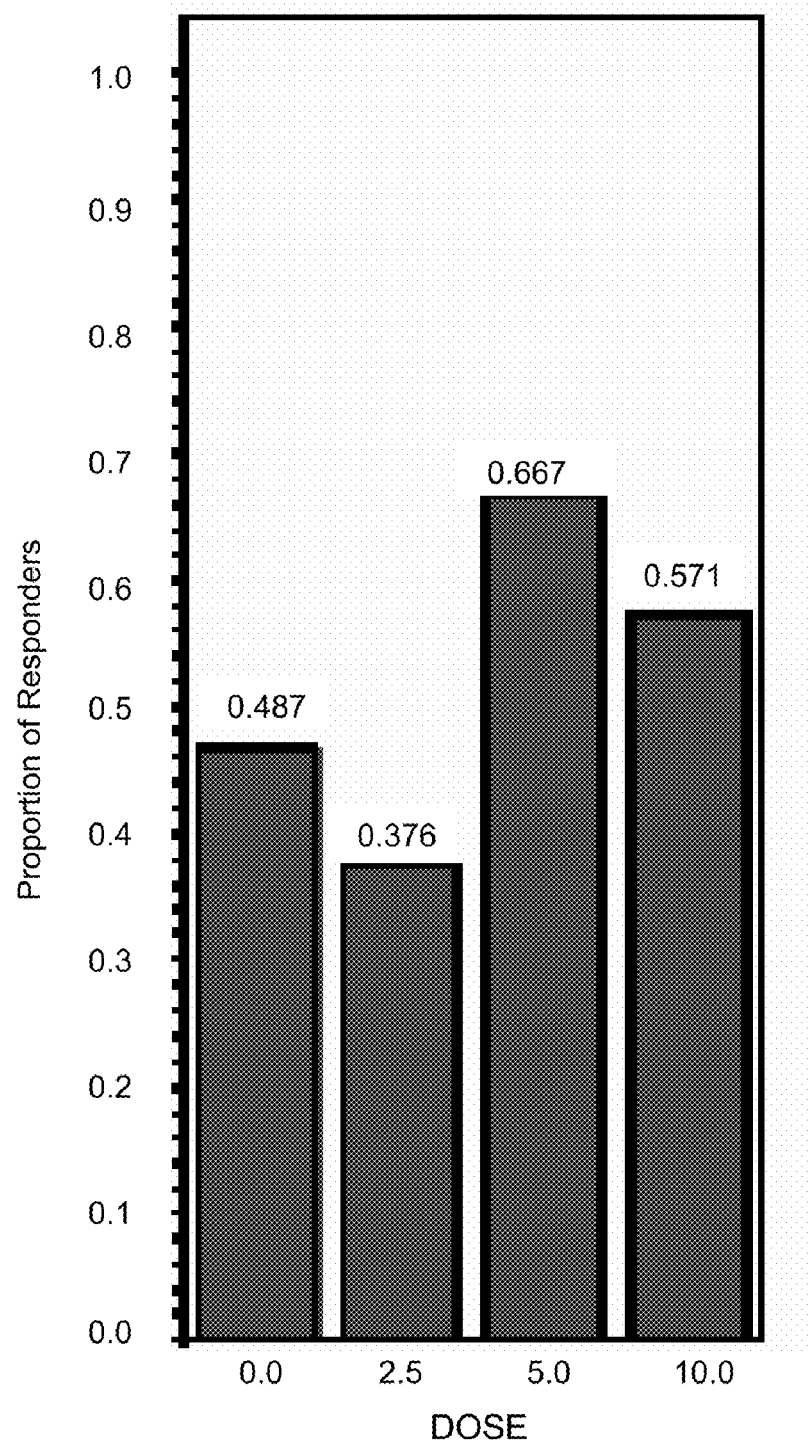
Figure 4N:
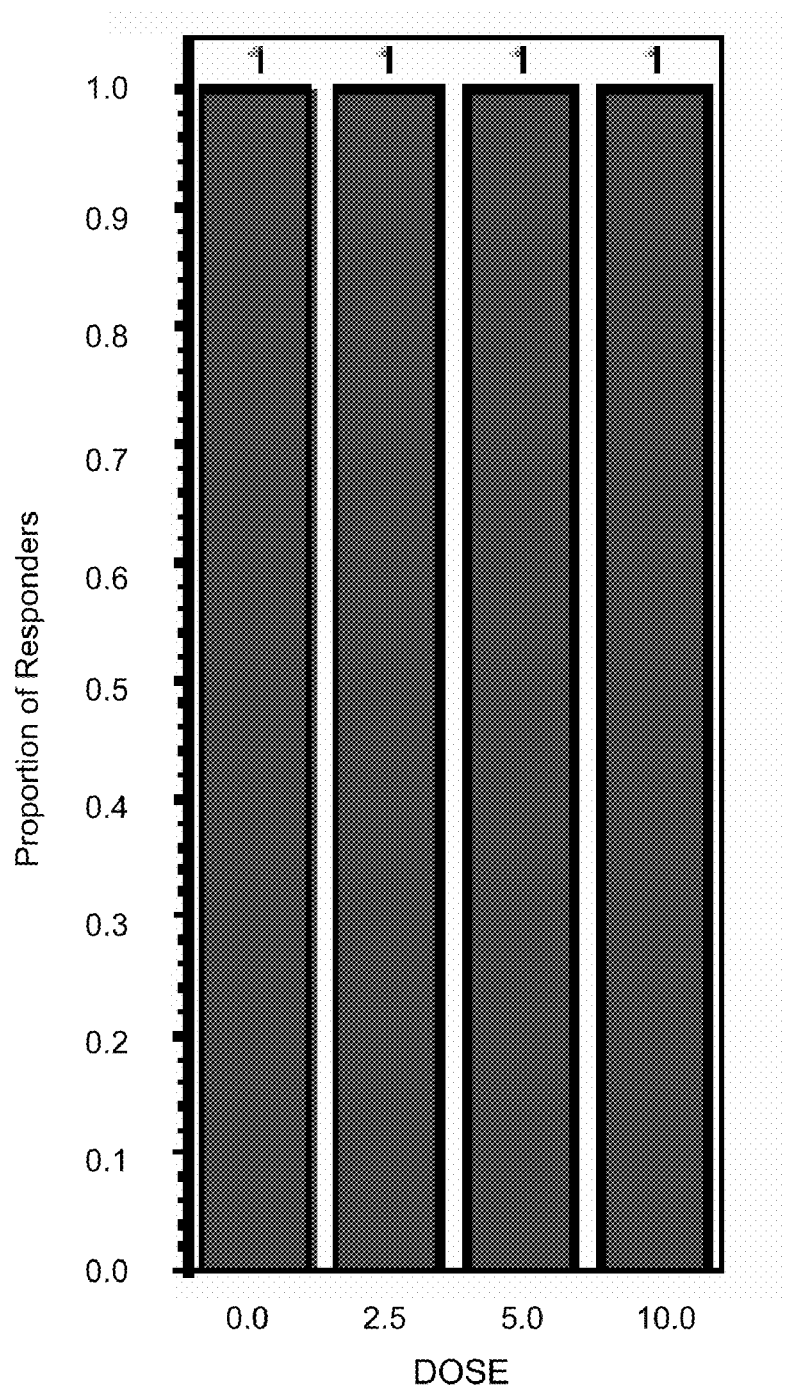
Figure 4O:
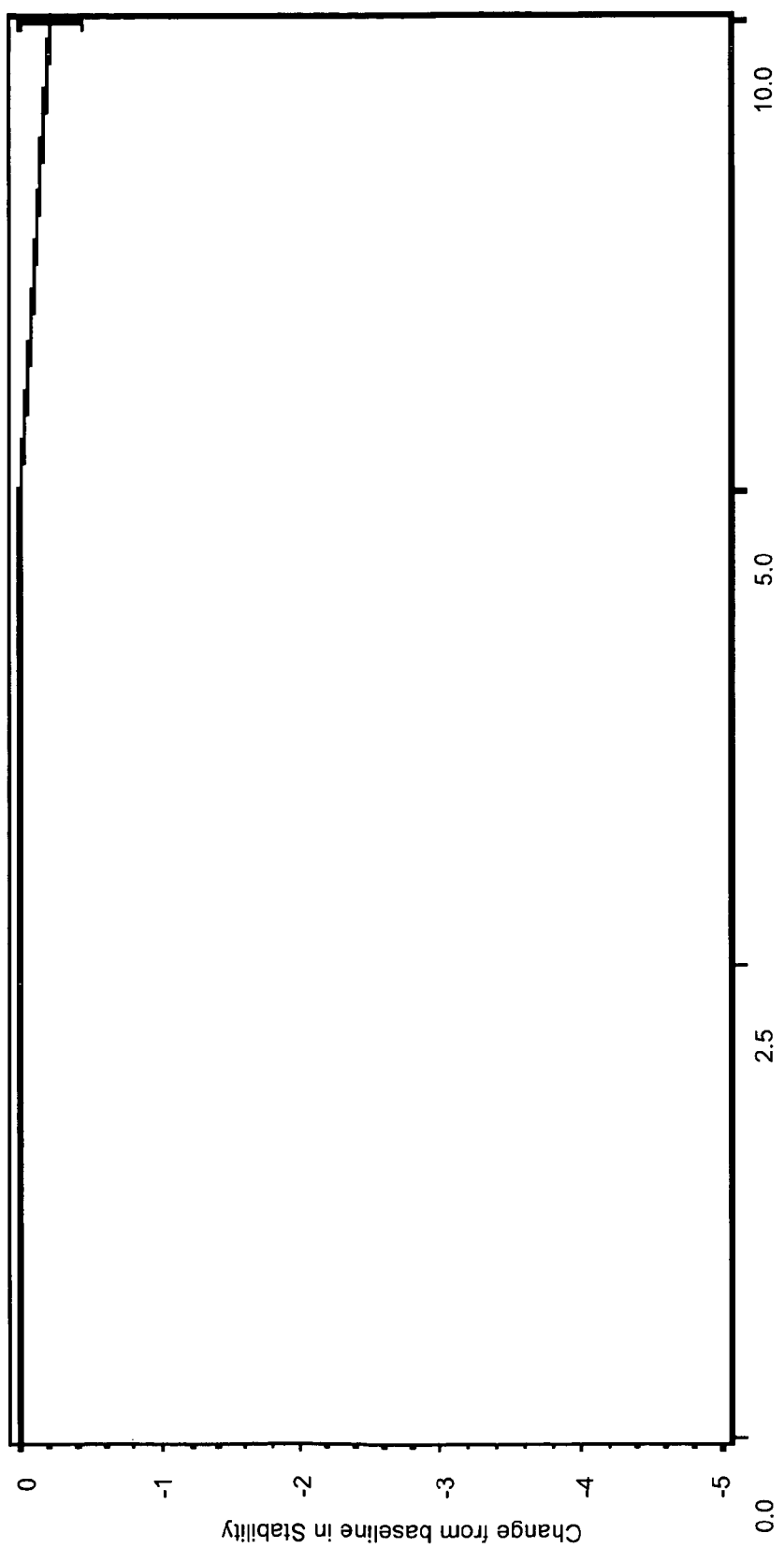
Figure 4P:
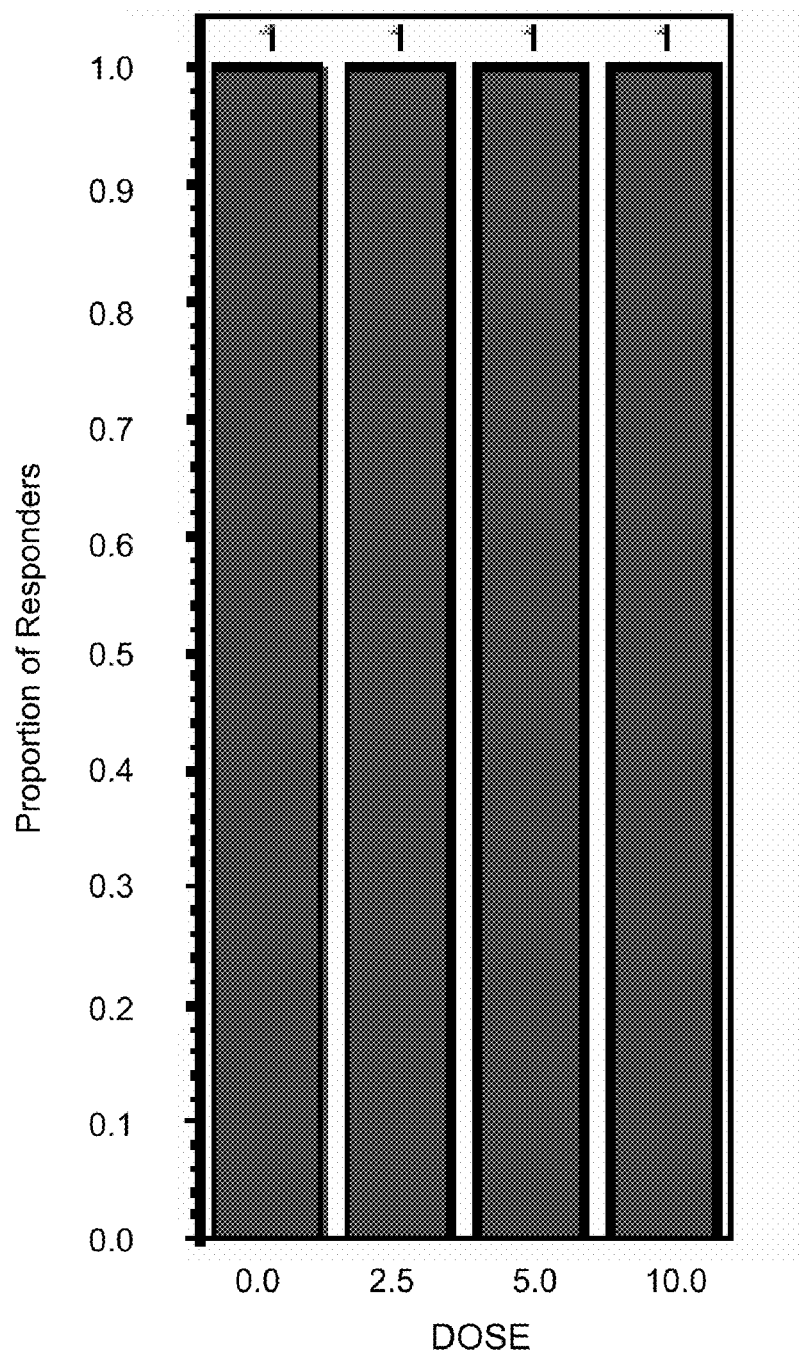
Figure 4Q:
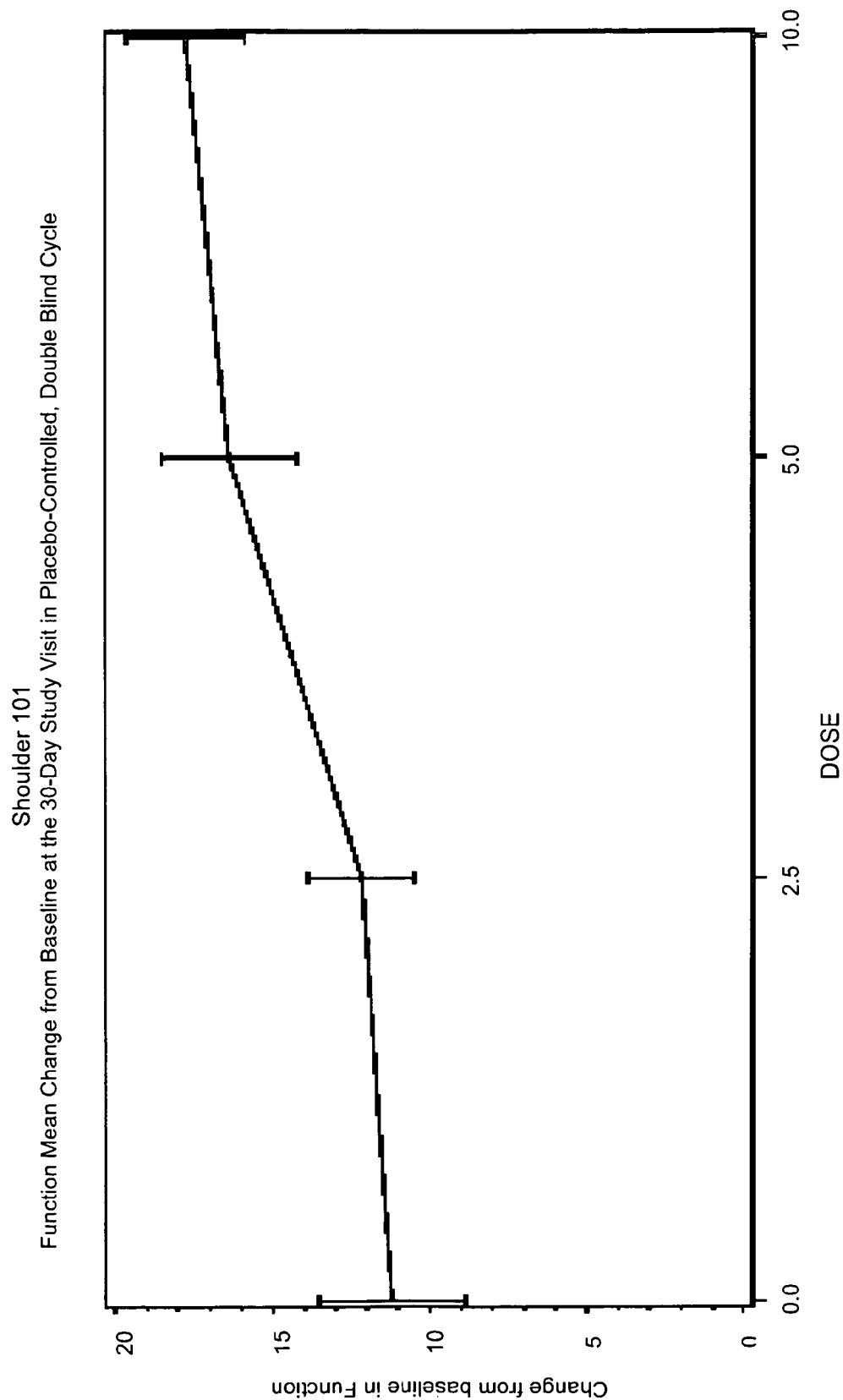
Figure 4R:
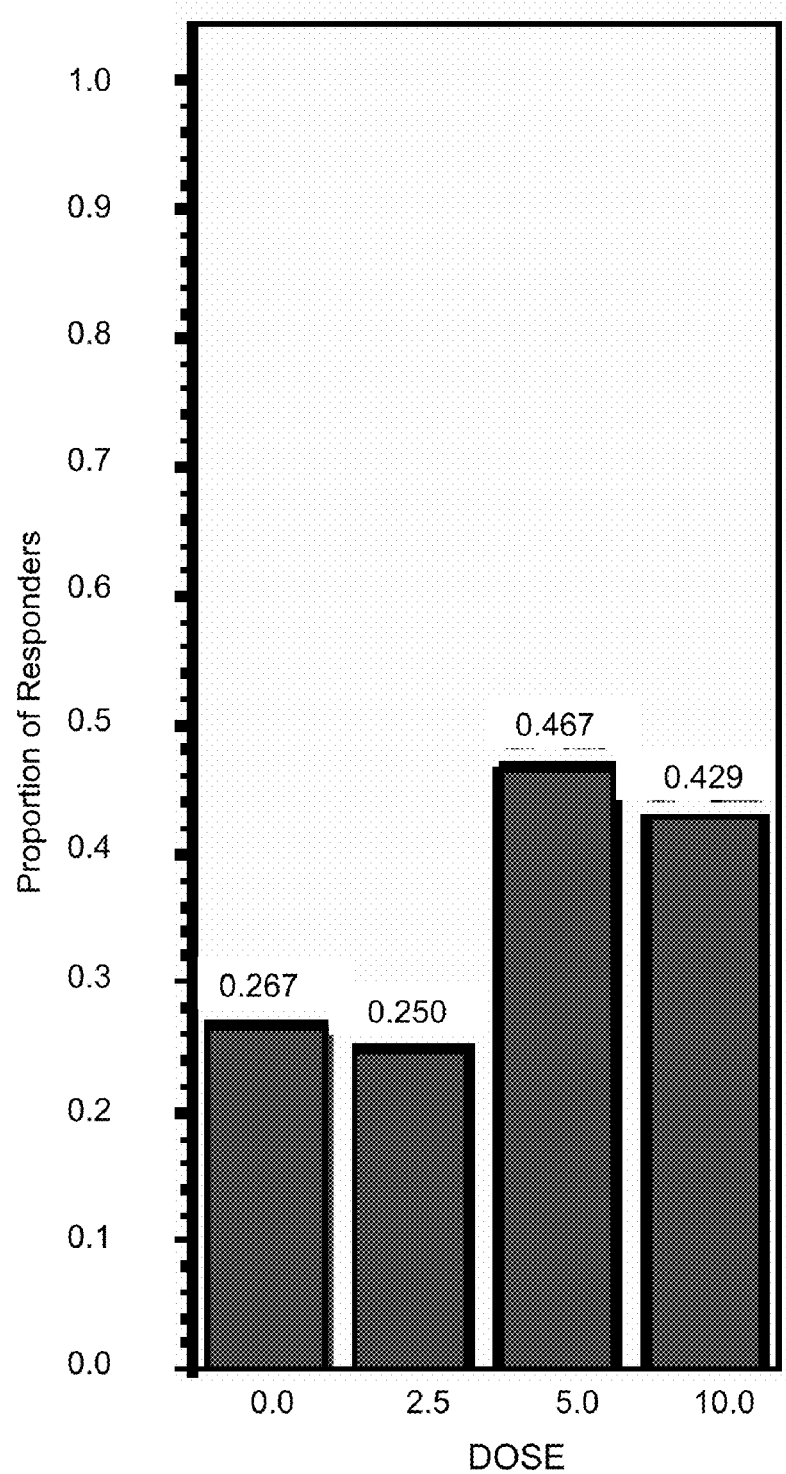
Figure 4S:
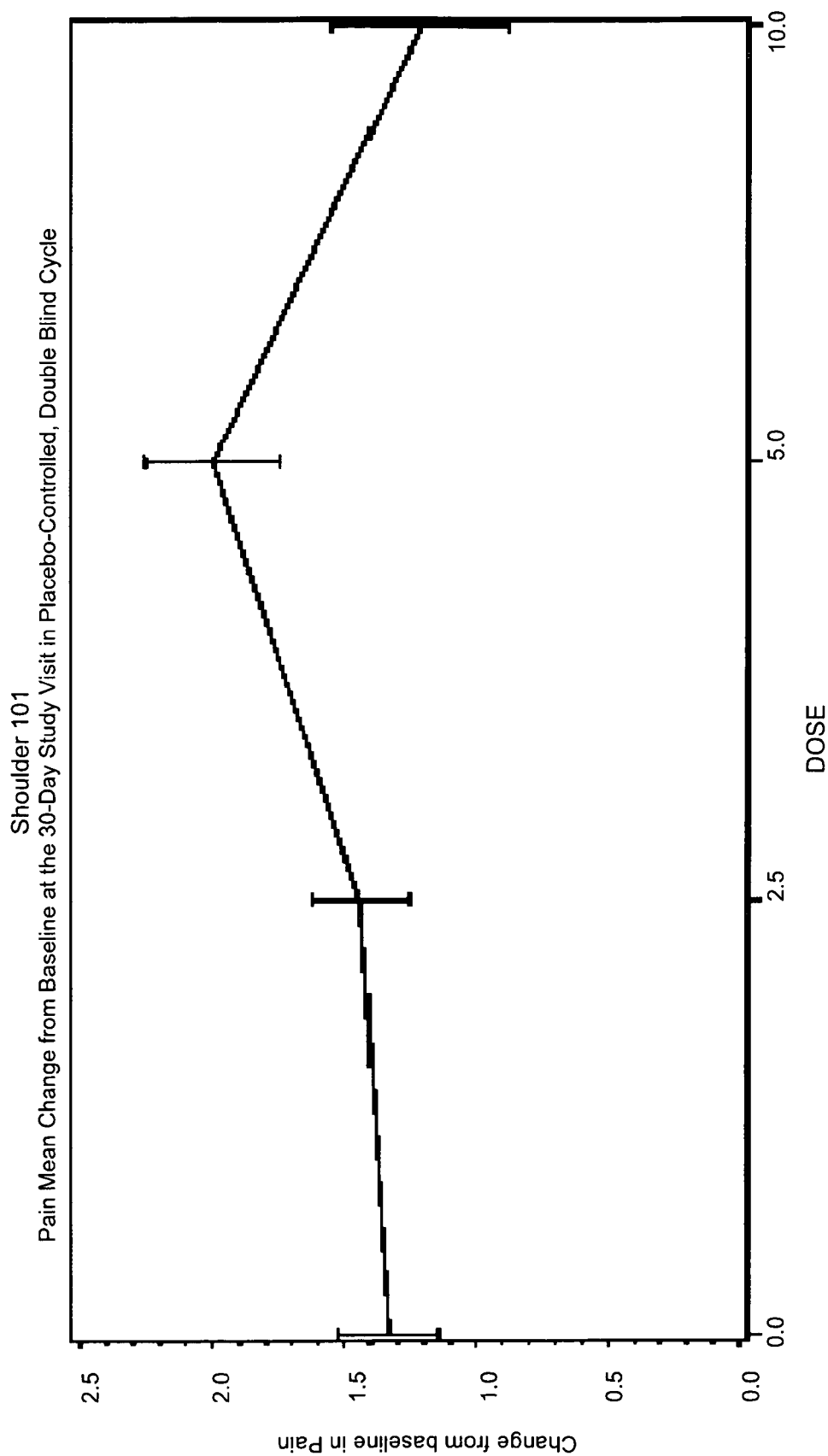
Figure 4T:
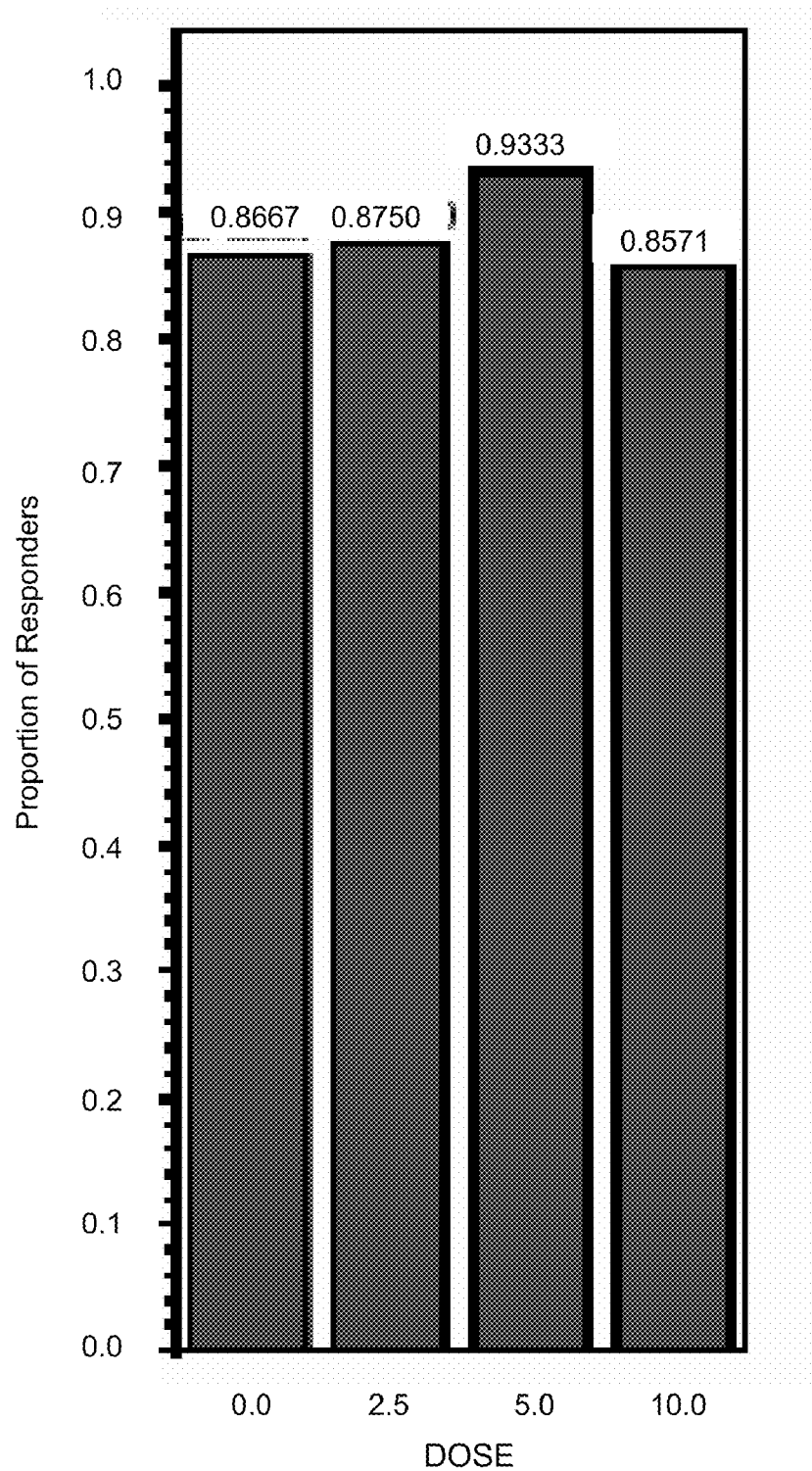
Figure 4U:
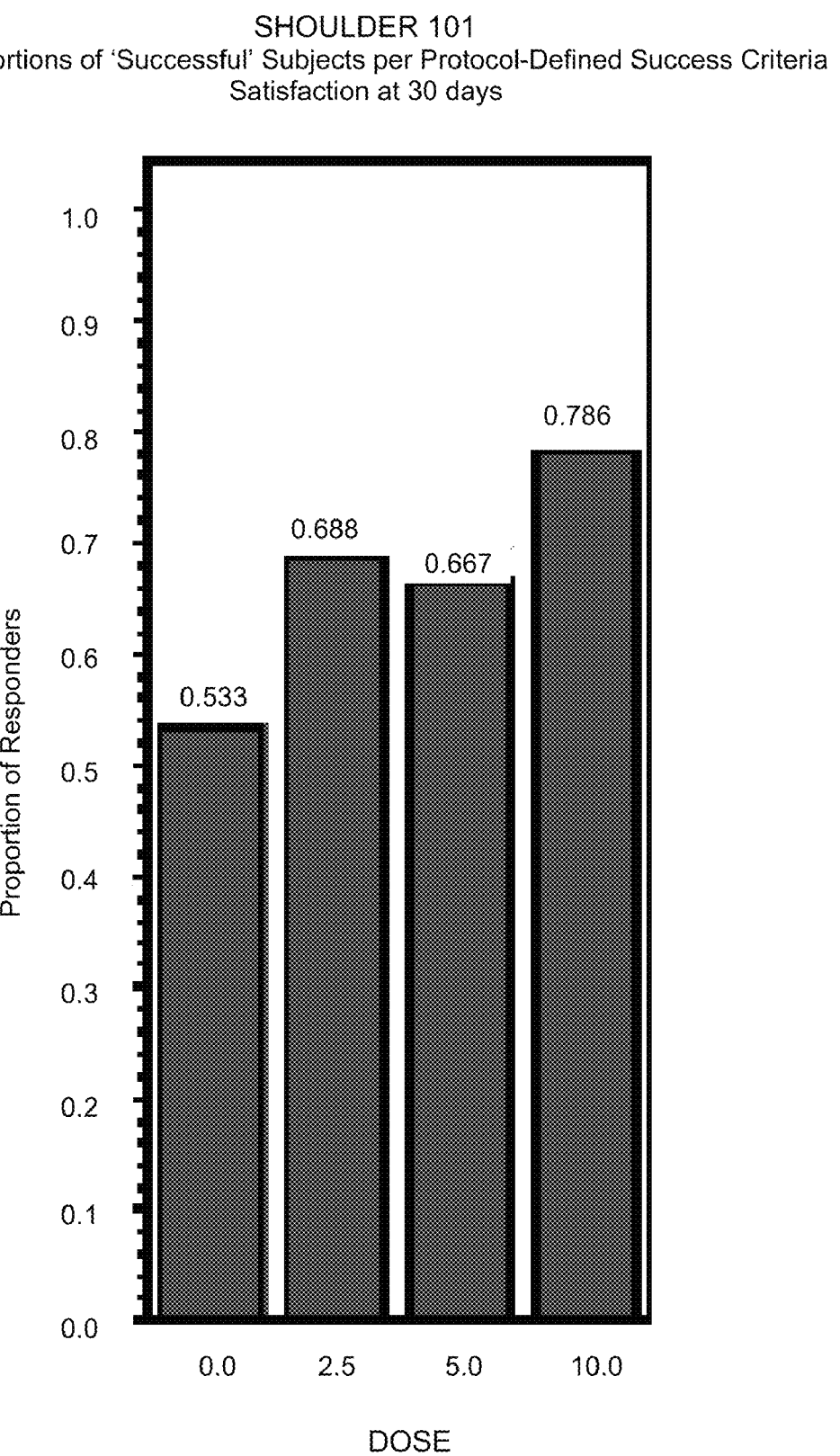
Figure 4V:
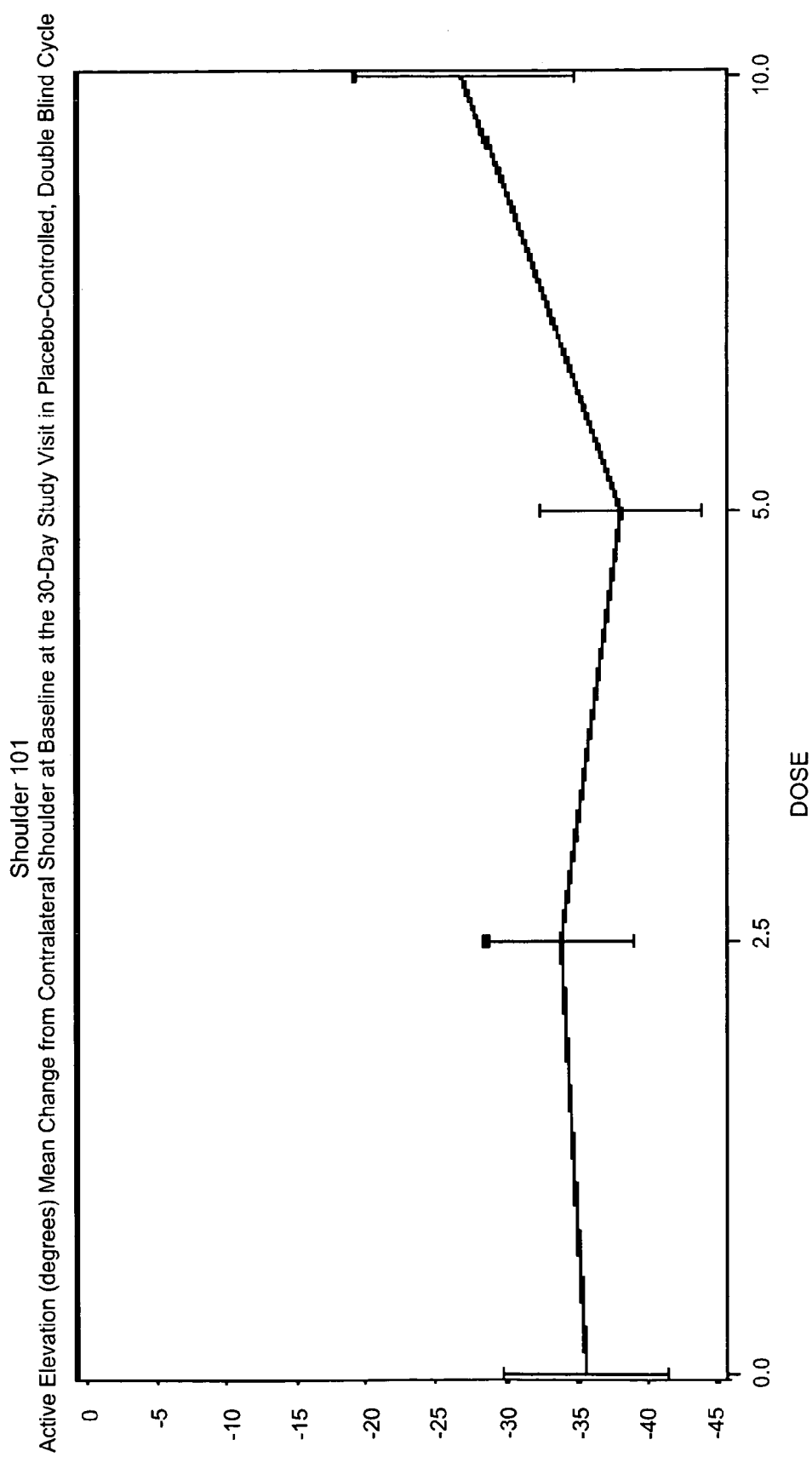
Figure 4W:
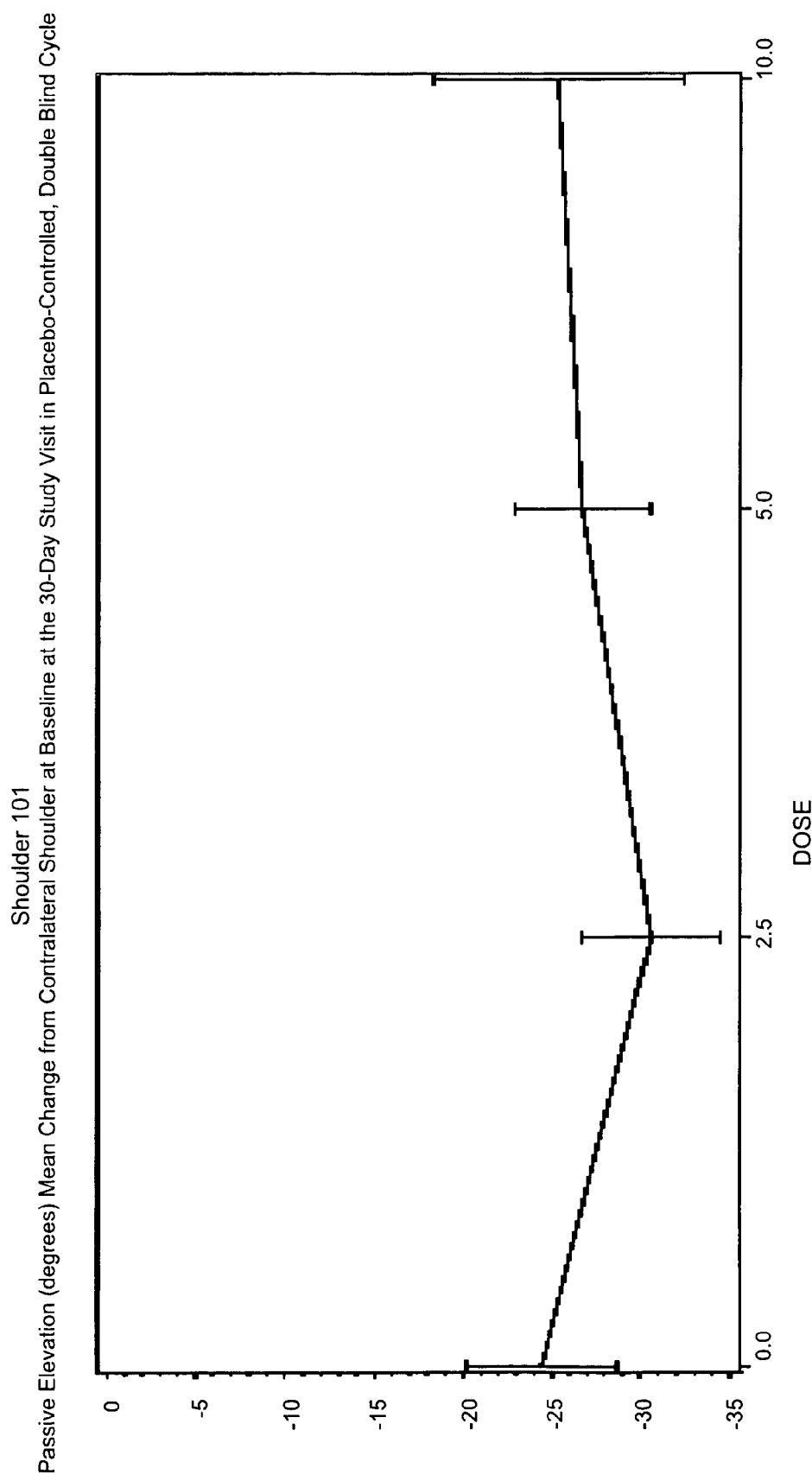
Figure 4X:
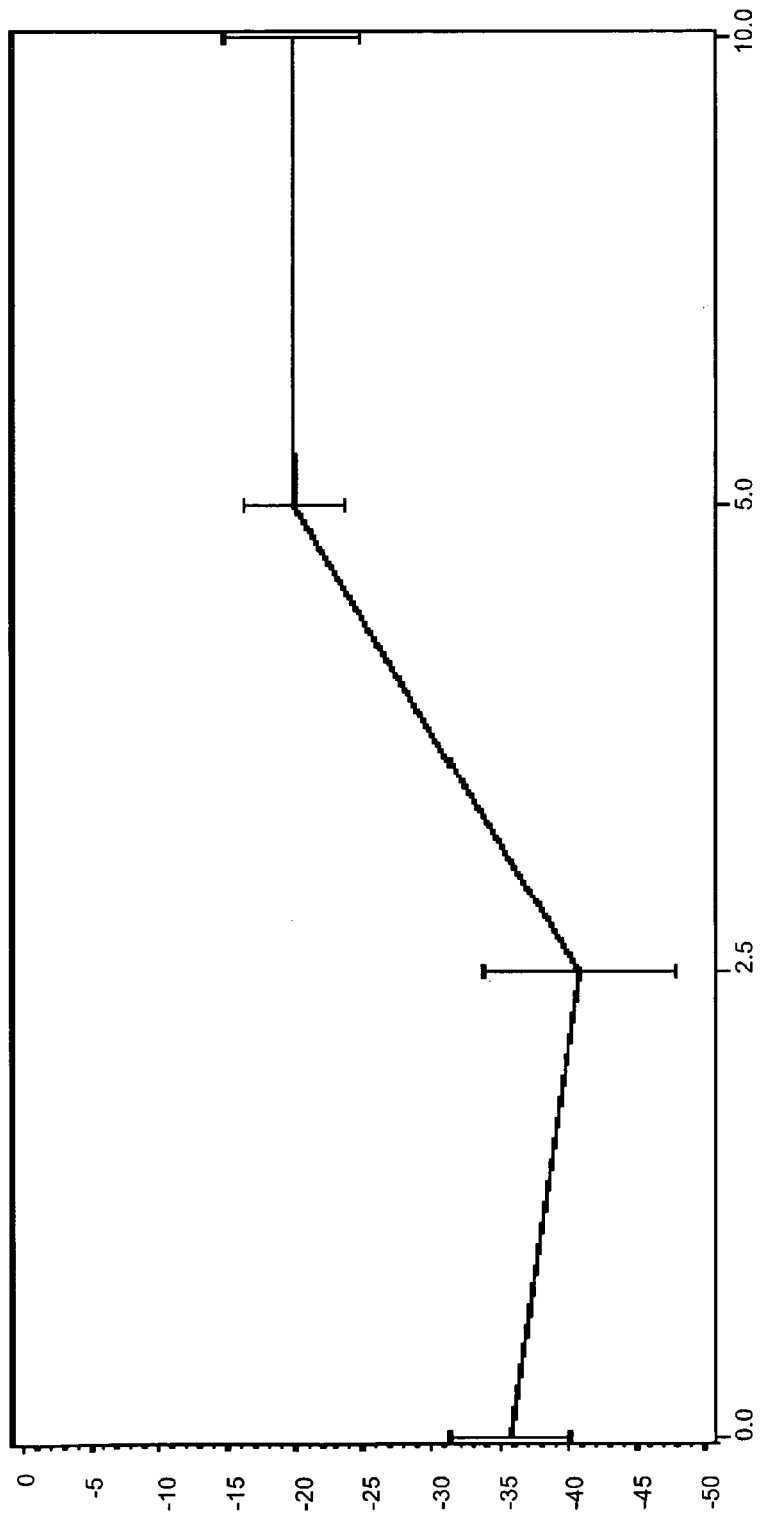
Figure 4Y:
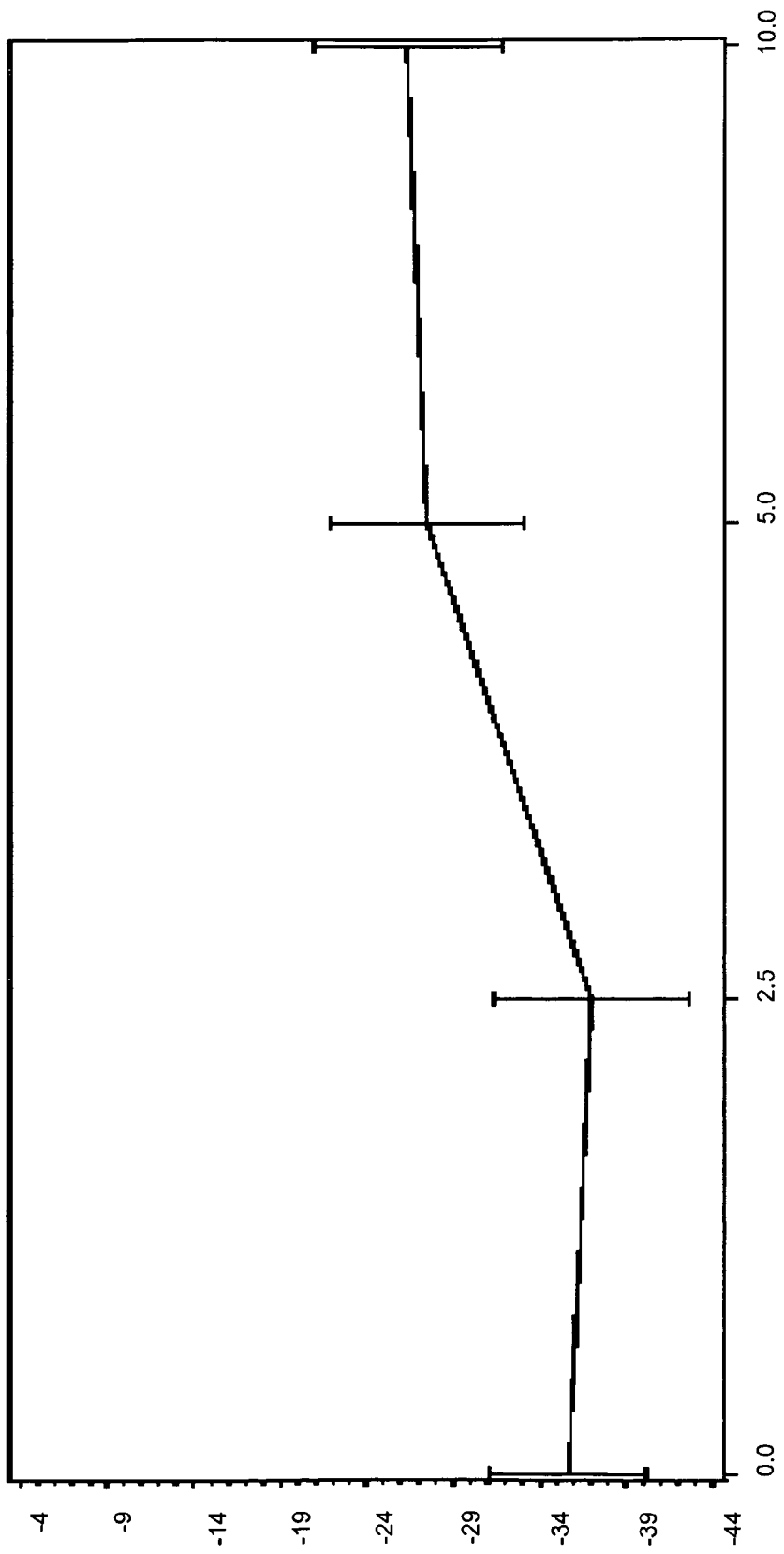
Figure 4Z:
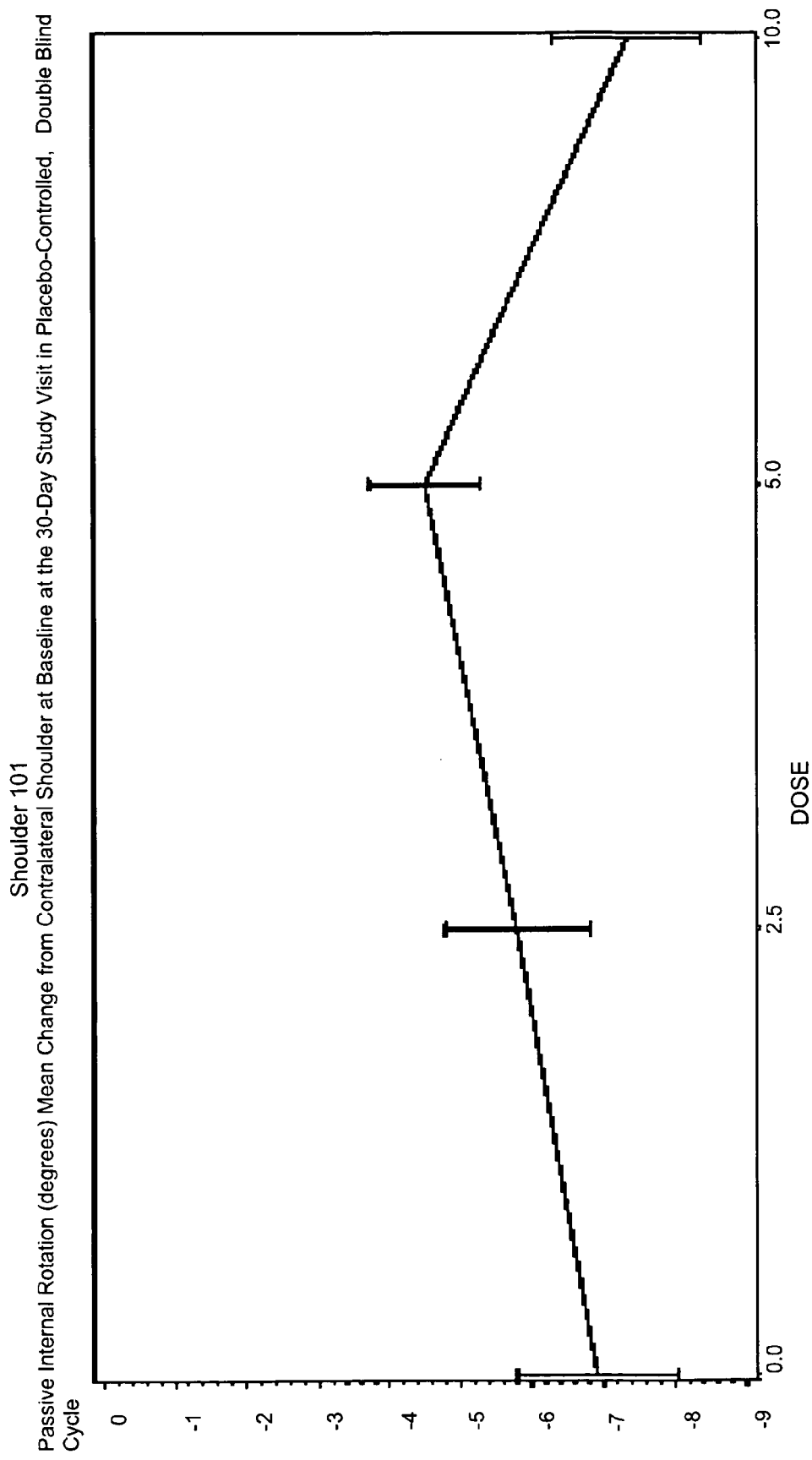
Figure 4A:
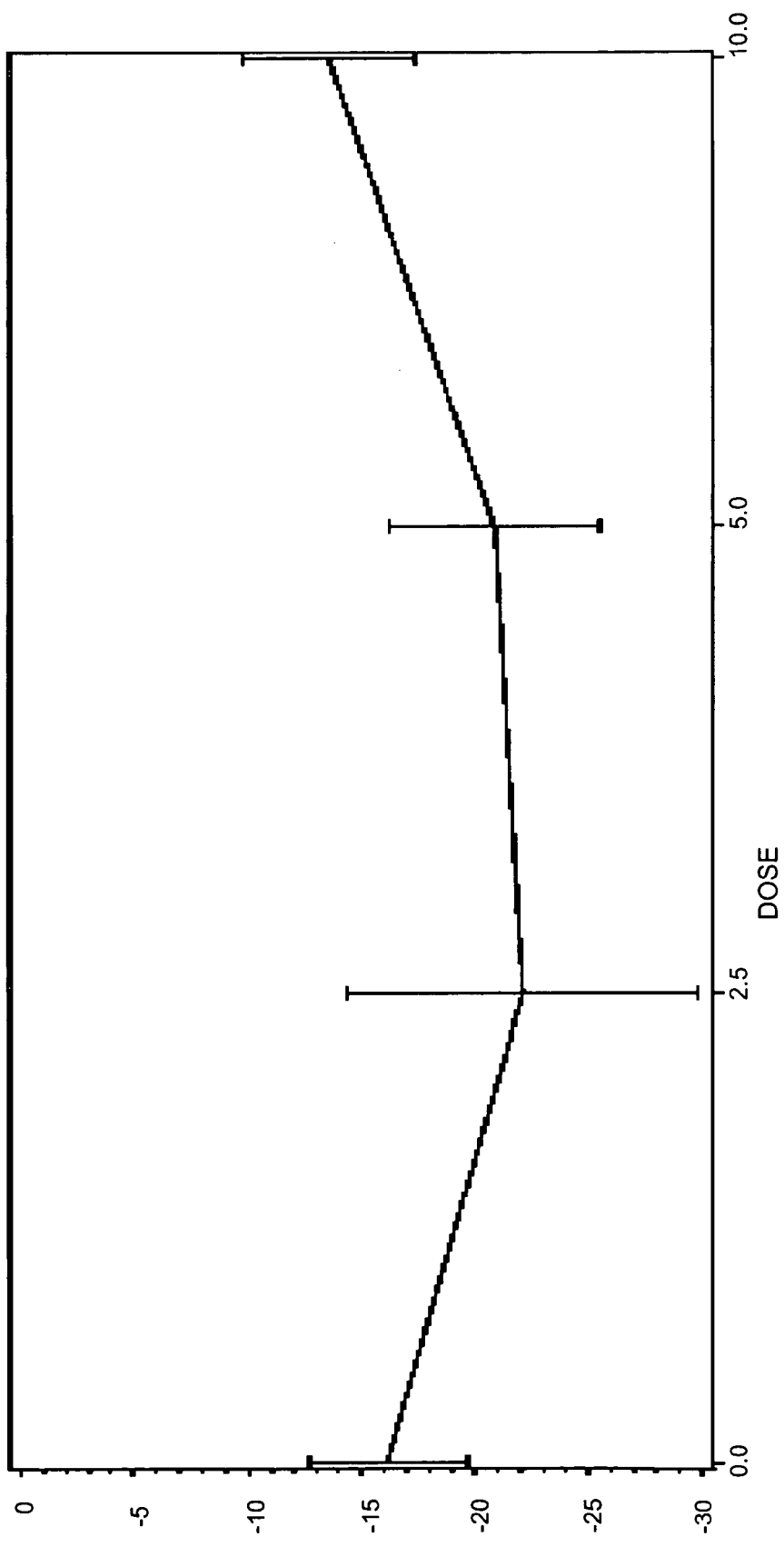
Figure 4B:
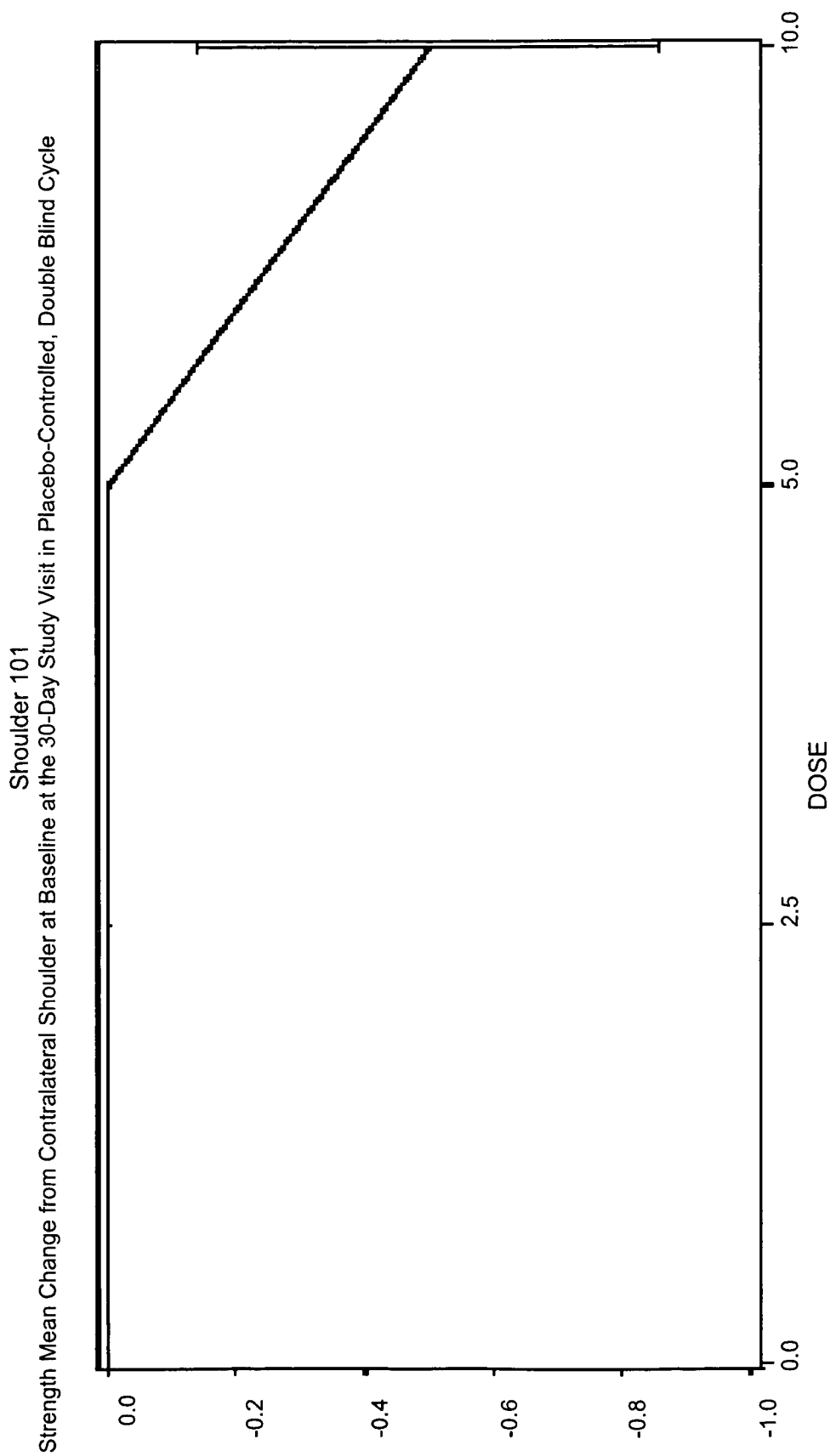
Figure 4C:
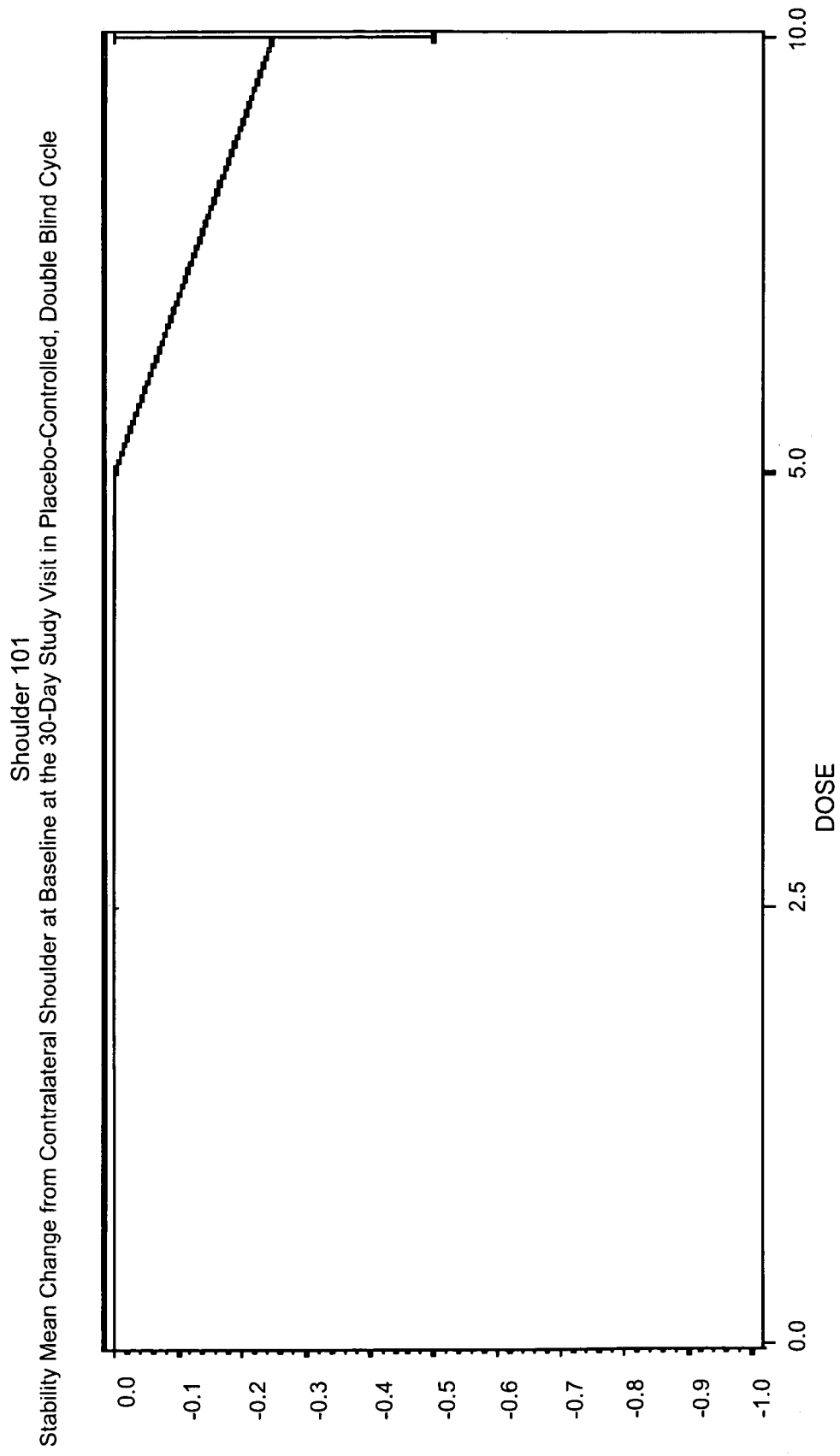
Figure 4E:
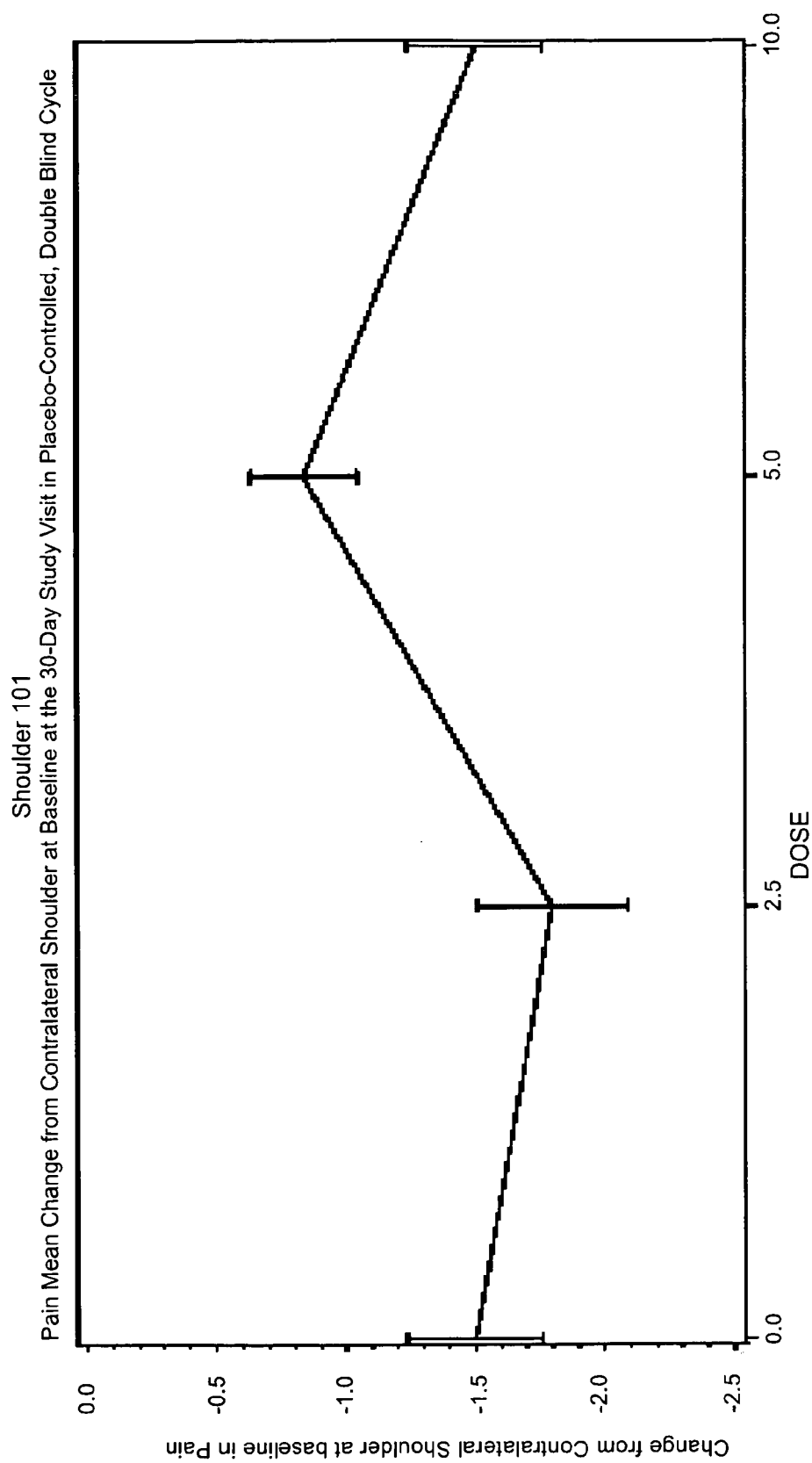

Twenty three patients had a second open label injection consisting of 0.58 mg collagenase. Improvements in active elevation, active external rotation, active internal rotation, passive elevation, passive elevation at the side, passive elevation at 90 degrees, function and pain score were significant (p<0.01) and dramatic, beginning atone day post the open label injection (FIG. 3). Baseline values are denoted in FIG. 3 at day 0. Normal values are on the y axis. At one month post injection, all parameters reached normal values, based on the means of the unaffected contralateral side. Slight improvements in all parameters occurred throughout the succeeding months of follow-up. Twenty patients went on to a third open label, 0.58 mg collagenase injection. Results in all parameters after one year were similar to those who received a second injection as delineated in FIG. 2. None of these patients were lost to 12 month follow-up.

Adverse events were local and minimal consisting of injection area tenderness and biceps ecchymosis. These resolved well in 7-14 days. There were no adverse immune events.

Discussion

This study has shown that collagenase injection for adhesive capsulitis is a novel method for early restoration of shoulder motion, function and pain resolution. The highest dose used (0.58 mg) trended to be the most effective in controlled study. However, it was apparent that a short series of injections using the 0.58 mg dose was more effective in open label study.

Additional Results

It is noted that the use of separate examples is not intended to imply that separate and distinct studies, rather than separate analysis of the results. The invention, of course, also relates to the use the collagenase formulations of the invention to achieve the results described in these results. The results of these studies also include the data presented in the following tables:

TABLE 1

Means ± standard deviation for endpoints at baseline and as the 30-day double-blind visit

|  |  | Plscebo (n = 15) | 2,500 u (n = 16) | 5,000 u (n = 15) | 10,000 u (n = 16) |
| --- | --- | --- | --- | --- | --- |
| Active elevation (degrees) | Treated shoulder at baseline | 112.9 ± 21.8 | 115.0 ± 16.2 | 109.1 ± 21.4 | 111.1 ± 20.3 |
|  | Contralateral Shoulder at baseline § | 168.0 ± 9.6 | 162.4 ± 14.2 | 170.8 ± 9.0 | 165.8 ± 16.0 |
|  | 30-day, double-blind observations | 125.2 ± 23.6 | 134.1 ± 22.8 | 127.8 ± 19.0 | 139.0 ± 22.1 |
| Active external rotation (degrees) | Treated shoulder at baseline | 25.2 ± 15.3 | 20.9 ± 17.1 | 29.7 ± 18.9 | 31.3 ± 14.6 |
|  | Contralateral Shoulder at baseline § | 81.7 ± 6.5 | 73.0 ± 19.8 | 78.5 ± 11.9 | 74.7 ± 16.0 |
|  | 30-day, double-blind observations | 41.4 ± 17.4 | 38.2 ± 20.5 | 54.8 ± 14.9 | 52.0 ± 16.2 |
| Active internal rotation (spise level) (degrees) | Treated shoulder at baseline | 4.9 ± 1.8 | 5.1 ± 2.4 | 5.3 ± 2.4 | 5.9 ± 2.8 |
|  | Contralateral Shoulder at baseline § | 15.3 ± 3.2 | 12.9 ± 4.1 | 13.8 ± 4.1 | 13.4 ± 2.8 |
|  | 30-day, double-blind observations | 7.5 ± 2.6 | 8.3 ± 3.6 | 8.3 ± 4.0 | 8.6 ± 4.0 |
| Passive elevation (degrees) | Treated shoulder at baseline | 127.7 ± 19.5 | 132.7 ± 17.7 | 125.6 ± 16.3 | 135.9 ± 14.4 |
|  | Contralateral Shoulder at baseline § | 175.2 ± 7.9 | 173.9 ± 9.0 | 176.2 ± 6.8 | 175.6 ± 9.4 |
|  | 30-day, double-blind observations | 143.3 ± 21.8 | 147.0 ± 20.6 | 144.9 ± 16.4 | 150.3 ± 21.4 |

TABLE 1-continued

Means ± standard deviation for endpoints at baseline and as the 30-day double-blind visit

|  |  | Placebo (n = 15) | 2,500 u (n = 16) | 5,000 u (n = 15) | 10,000 u (n = 16) |
|---|---|---|---|---|---|
| Passive external rotation (degrees) | Treated shoulder at baseline | 32.8 ± 22.3 | 23.3 ± 15.5 | 29.5 ± 14.8 | 26.7 ± 18.9 |
|  | Contralateral Shoulder at baseline § | 89.6 ± 1.4 | 80.3 ± 17.1 | 87.9 ± 5.8 | 83.8 ± 9.3 |
|  | 30-day, double-blind observations | 47.3 ± 19.8 | 46.6 ± 22.9 | 56.5 ± 22.2 | 58.7 ± 22.0 |
| Passive external elevation @ 90° (degrees) | Treated shoulder at baseline | 68.0 ± 16.1 | 70.3 ± 34.5 | 67.0 ± 18.1 | 72.3 ± 13.2 |
|  | Contralateral Shoulder at baseline § | 102.1 ± 5.1 | 99.6 ± 15.4 | 110.7 ± 12.6 | 102.3 ± 7.6 |
|  | 30-day, double-blind observations | 83.3 ± 13.6 | 82.1 ± 13.5 | 88.7 ± 11.8 | 88.9 ± 10.1 |
| Function score (0-60 scale) | Treated shoulder at baseline | 31.2 ± 9.3 | 32.0 ± 7.1 | 32.9 ± 7.5 | 31.9 ± 6.8 |
|  | Contralateral Shoulder at baseline § | 60.0 ± 0.0 | 60.0 ± 0.0 | 60.0 ± 0.0 | 60.0 ± 0.0 |
|  | 30-day, double-blind observations | 42.4 ± 12.4 | 44.2 ± 9.8 | 49.3 ± 8.8 | 49.7 ± 7.5 |
| Pain score (0-5 scale) | Treated shoulder at baseline | 2.0 ± 0.8 | 1.9 ± 0.9 | 1.9 ± 0.8 | 2.3 ± 1.0 |
|  | Contralateral Shoulder at baseline § | 5.0 ± 0.0 | 5.0 ± 0.0 | 5.0 ± 0.0 | 5.0 ± 0.0 |
|  | 30-day, double-blind observations | 3.3 ± 0.9 | 3.8 ± 0.9 | 3.9 ± 0.9 | 3.5 ± 0.9 |

§ For contralateral shoulder at baseline, n = 12, 10, 12, and 12 for respectively, placebo, 2,500 u, 5000 u, and 10,000 u treatments.

TABLE 2

Means ± standard deviation for endpoints at the 30-day visit after the first and second open-label treatments

|  | Open-label treatment of 10,000 u | Randomization group | | | |
|---|---|---|---|---|---|
|  |  | Placebo | 2,500 u | 5,000 u | 10,000 u |
| Active elevation (degrees) | First § | 143.6 ± 24.5 | 146.8 ± 15.5 | 143.2 ± 18.8 | 148.8 ± 13.2 |
|  | Second § | 141.7 ± 18.3 | 144.1 ± 12.7 | 152.5 ± 8.7 | 155.2 ± 4.3 |
| Active external rotation (degrees) | First § | 60.2 ± 20.1 | 46.8 ± 17.1 | 64.8 ± 18.7 | 54.8 ± 14.7 |
|  | Second § | 62.6 ± 19.2 | 47.1 ± 16.6 | 61.3 ± 12.2 | 62.0 ± 13.7 |
| Active internal rotation (spice level) (degrees) | First § | 10.2 ± 9.6 | 9.2 ± 5.2 | 9.8 ± 4.2 | 10.7 ± 4.9 |
|  | Second § | 10.4 ± 4.5 | 8.4 ± 3.6 | 12.0 ± 7.6 | 9.2 ± 2.3 |
| Passive elevation (degrees) | First § | 156.7 ± 22.7 | 154.3 ± 16.1 | 156.1 ± 19.8 | 158.1 ± 12.6 |
|  | Second § | 158.7 ± 16.5 | 152.9 ± 14.0 | 167.0 ± 9.5 | 164.8 ± 8.5 |
| Passive external rotation (degrees) | First § | 69.5 ± 22.1 | 56.9 ± 24.7 | 68.9 ± 20.5 | 60.9 ± 17.5 |
|  | Second § | 74.0 ± 22.2 | 53.9 ± 22.5 | 64.0 ± 16.8 | 62.3 ± 7.7 |
| Passive external elevation @ 90° (degrees) | First § | 93.7 ± 15.9 | 86.5 ± 9.7 | 96.6 ± 9.9 | 93.4 ± 14.0 |
|  | Second § | 95.7 ± 16.4 | 85.7 ± 8.4 | 101.8 ± 7.9 | 98.7 ± 5.6 |
| Function score (0-60 scale) | First § | 51.4 ± 9.1 | 51.2 ± 6.3 | 51.2 ± 8.5 | 52.4 ± 7.0 |
|  | Second § | 52.6 ± 9.9 | 53.4 ± 3.8 | 52.0 ± 10.8 | 53.7 ± 2.7 |
| Pain score (0-5 scale) | First § | 3.9 ± 1.0 | 4.3 ± 0.5 | 4.1 ± 0.3 | 4.1 ± 0.9 |
|  | Second § | 3.7 ± 1.0 | 4.1 ± 0.7 | 4.0 ± 0.8 | 4.3 ± 0.5 |

§ For First open label treatment, n = 13, 12, 9, and 10 for, respectively, placebo, 2,500 u, 5000 u, and 10,000 u treatments, except for active elevation and passive elevation for which n = 9 for the 5000 u group.
§ For second open label treatment, n = 7, 7, 4, and 6 for, respectively, placebo, 2,500 u, 5000 u, and 10,000 u treatments.

TABLE 3

Mean change from baseline contralateral shoulder for endpoints at the 30-day visit after the first and second open-label treatments

|  | Open-label treatment of 10,000 u | Randomization group | | | |
|---|---|---|---|---|---|
|  |  | Placebo | 2,500 u | 5,000 u | 10,000 u |
| Active elevation (degrees) | First § | −13.9 | −18.1 | −24.1 | −12.4 |
|  | Second § | −13.5 | −15.2 | −10.0 | −9.0 |
| Active external rotation (degrees) | First § | −15.6 | −32.1 | −9.6 | −15.6 |
|  | Second § | −15.5 | −26.8 | −18.0 | −6.8 |
| Active internal rotation (spice level) (degrees) | First § | −3.7 | −3.0 | −3.3 | −5.4 |
|  | Second § | −3.3 | −4.6 | −1.0 | −5.6 |
| Passive elevation (degrees) | First § | −7.8 | −21.5 | −14.1 | −17.3 |
|  | Second § | −5.0 | −19.2 | −7.0 | −9.6 |
| Passive external rotation (degrees) | First § | −11.0 | −28.1 | −16.4 | −23.3 |
|  | Second § | −2.5 | −21.0 | −18.0 | −20.2 |
| Passive external elevation @ 90° (degrees) | First § | −1.9 | −11.6 | −14.1 | −6.0 |
|  | Second § | 0.5 | −11.2 | −16.0 | −6.6 |
| Function score (0-60 scale) | First § | −4.6 | −9.5 | −5.4 | −8.1 |
|  | Second § | −3.0 | −7.0 | −2.7 | −2.6 |
| Parts score (0-5 scale) | First § | −0.8 | −0.8 | −0.9 | −0.9 |
|  | Second § | −0.8 | −0.6 | −0.7 | −0.8 |

§ For First open label treatment, n = 10, 8, 8, and 8 for, respectively, placebo, 2500 u, 5000 u, and 10,000 u treatments.
§ For second open label treatment, n = 4, 5, 3, and 5 for, respectively, placebo, 2,500 u, 5000 u, and 10,000 u treatments.

TABLE 4

Change from baseline (except success rate) at the 30-day study visit
Active elevation

| Treatment cycle | Incremental dose | n | Protocol-defined success rate (%) | p-value vs placebo | Median (degrees) | p-value vs placebo | Mean (degrees) | p-value vs placebo |
|---|---|---|---|---|---|---|---|---|
| \multicolumn{9}{c}{Placebo-controlled, double-blind study phase} |
| 1 | 0 (Placebo) | 15 | 6.7 |  | 9.0 |  | 12.27 |  |
| 1 | 2,500 | 16 | 12.5 | 1.00 | 19.5 | 0.15 | 19.13 | 0.19 |
| 1 | 5,000 | 15 | 0.0 | 1.00 | 22.0 | 0.30 | 18.73 | 0.25 |
| 1 | 10,000 | 14 | 14.3 | 0.60 | 26.0 | 0.02 | 27.79 | 0.02 |
| \multicolumn{9}{c}{Open-label study phase} |
| 2 | 10,000 | 45 |  |  | 35.0 |  | 33.98 |  |
| 3 | 10,000 | 24 |  |  | 42.0 |  | 39.08 |  |
| 4 | 10,000 | 3 |  |  | 17.0 |  | 28.33 |  |
| 5 | 10,000 | 2 |  |  | 17.5 |  | 17.50 |  |

TABLE 5

Change from baseline (except success rate) at the 30-day study visit
Passive elevation

| Treatment cycle | Incremental dose | n | Protocol-defined success rate (%) | p-value vs placebo | Median (degrees) | p-value vs placebo | Mean (degrees) | p-value vs placebo |
|---|---|---|---|---|---|---|---|---|
| \multicolumn{9}{c}{Placebo-controlled, double-blind study phase} |
| 1 | 0 (Placebo) | 15 | 26.7 |  | 15.0 |  | 15.67 |  |
| 1 | 2,500 | 16 | 31.3 | 1.00 | 17.0 | 0.77 | 14.31 | 0.79 |
| 1 | 5,000 | 15 | 20.0 | 1.00 | 20.0 | 0.87 | 19.27 | 0.53 |
| 1 | 10,000 | 14 | 28.6 | 1.00 | 16.5 | 0.66 | 14.43 | 0.83 |
| \multicolumn{9}{c}{Open-label study phase} |
| 2 | 10,000 | 44 |  |  | 30.0 |  | 27.56 |  |
| 3 | 10,000 | 24 |  |  | 35.5 |  | 31.00 |  |
| 4 | 10,000 | 3 |  |  | 17.0 |  | 25.67 |  |
| 5 | 10,000 | 2 |  |  | 20.5 |  | 20.50 |  |

TABLE 6

Change from baseline (except success rate) at the 30-day study visit
Active ER at side

| Treatment cycle | Incremental dose | n | Protocol-defined success rate (%) | p-value vs placebo | Median (degrees) | p-value vs placebo | Mean (degrees) | p-value vs placebo |
|---|---|---|---|---|---|---|---|---|
| \multicolumn{9}{c}{Placebo-controlled, double-blind study phase} |
| 1 | 0 (Placebo) | 15 | 46.7 |  | 10.0 |  | 16.20 |  |
| 1 | 2,500 | 16 | 37.5 | 0.72 | 19.0 | 0.62 | 17.25 | 0.80 |
| 1 | 5,000 | 15 | 73.3 | 0.26 | 27.0 | 0.12 | 25.13 | 0.08 |
| 1 | 10,000 | 14 | 71.4 | 0.26 | 18.5 | 0.41 | 20.71 | 0.44 |
| \multicolumn{9}{c}{Open-label study phase} |
| 2 | 10,000 | 44 |  |  | 28.0 |  | 30.55 |  |
| 3 | 10,000 | 24 |  |  | 34.0 |  | 36.79 |  |
| 4 | 10,000 | 3 |  |  | 36.0 |  | 36.33 |  |
| 5 | 10,000 | 2 |  |  | 30.5 |  | 30.50 |  |

TABLE 7

Change from baseline (except success rate) at the 30-day study visit
Passive ER at side

| Treatment cycle | Incremental dose | n | Protocol-defined success rate (%) | p-value vs placebo | Median (degrees) | p-value vs placebo | Mean (degrees) | p-value vs placebo |
|---|---|---|---|---|---|---|---|---|
| Placebo-controlled, double-blind study phase ||||||||| 
| 1 | 0 (Placebo) | 15 | 60.0 | | 7.0 | | 14.47 | |
| 1 | 2,500 | 16 | 56.3 | 1.00 | 20.5 | 0.28 | 23.31 | 0.27 |
| 1 | 5,000 | 15 | 66.7 | 1.00 | 26.0 | 0.13 | 27.00 | 0.11 |
| 1 | 10,000 | 14 | 71.4 | 0.70 | 31.5 | 0.05 | 32.00 | 0.03 |
| Open-label study phase |||||||||
| 2 | 10,000 | 44 | | | 34.5 | | 35.80 | |
| 3 | 10,000 | 24 | | | 31.5 | | 35.54 | |
| 4 | 10,000 | 3 | | | 21.0 | | 23.33 | |
| 5 | 10,000 | 2 | | | 19.5 | | 19.50 | |

TABLE 8

Change from baseline (except success rate) at the 30-day study visit
IR spinal level

| Treatment cycle | Incremental dose | n | Protocol-defined success rate (%) | p-value vs placebo | Median (degrees) | p-value vs placebo | Mean (degrees) | p-value vs placebo |
|---|---|---|---|---|---|---|---|---|
| Placebo-controlled, double-blind study phase |||||||||
| 1 | 0 (Placebo) | 15 | 26.7 | | 3.0 | | 2.67 | |
| 1 | 2,500 | 16 | 50.0 | 0.27 | 4.0 | 0.56 | 3.13 | 0.60 |
| 1 | 5,000 | 15 | 40.0 | 0.70 | 2.0 | 0.88 | 3.07 | 0.66 |
| 1 | 10,000 | 14 | 42.9 | 0.45 | 2.0 | 0.88 | 2.64 | 0.98 |
| Open-label study phase |||||||||
| 2 | 10,000 | 44 | | | 5.0 | | 5.16 | |
| 3 | 10,000 | 24 | | | 5.0 | | 5.50 | |
| 4 | 10,000 | 3 | | | 4.0 | | 6.33 | |
| 5 | 10,000 | 2 | | | 3.5 | | 3.50 | |

TABLE 9

Change from baseline (except success rate) at the 30-day study visit
Passive ER at 90°

| Treatment cycle | Incremental dose | n | Protocol-defined success rate (%) | p-value vs placebo | Median (degrees) | p-value vs placebo | Mean (degrees) | p-value vs placebo |
|---|---|---|---|---|---|---|---|---|
| Placebo-controlled, double-blind study phase |||||||||
| 1 | 0 (Placebo) | 15 | 46.7 | | 15.0 | | 15.33 | |
| 1 | 2,500 | 16 | 37.5 | 0.72 | 14.5 | 0.83 | 11.75 | 0.53 |
| 1 | 5,000 | 15 | 66.7 | 0.46 | 20.0 | 0.22 | 21.67 | 0.30 |
| 1 | 10,000 | 14 | 57.1 | 0.72 | 15.0 | 0.73 | 16.57 | 0.82 |
| Open-label study phase |||||||||
| 2 | 10,000 | 44 | | | 21.0 | | 23.80 | |
| 3 | 10,000 | 24 | | | 20.0 | | 23.17 | |
| 4 | 10,000 | 3 | | | 15.0 | | 20.33 | |
| 5 | 10,000 | 2 | | | 15.0 | | 15.00 | |

TABLE 10

Change from baseline (except success rate) at the 30-day study visit
Strength

| Treatment cycle | Incremental dose | n | Protocol-defined success rate (%) | p-value vs placebo | Median | p-value vs placebo | Mean | p-value vs placebo |
|---|---|---|---|---|---|---|---|---|
| Placebo-controlled, double-blind study phase ||||||||||
| 1 | 0 (Placebo) | 15 | 100.0 | | 0 | | 0 | |
| 1 | 2,500 | 16 | 100.0 | | 0 | 1.00 | 0 | |
| 1 | 5,000 | 15 | 100.0 | | 0 | 0.18 | 0.33 | 0.16 |
| 1 | 10,000 | 14 | 100.0 | | 0 | 0.16 | −0.43 | 0.16 |
| Open-label study phase ||||||||||
| 2 | 10,000 | 44 | | | 0 | | −0.05 | |
| 3 | 10,000 | 24 | | | 0 | | −0.08 | |
| 4 | 10,000 | 3 | | | 0 | | 0 | |
| 5 | 10,000 | 2 | | | 0 | | 0 | |

TABLE 11

Change from baseline (except success rate) at the 30-day study visit
Stability

| Treatment cycle | Incremental dose | n | Protocol-defined success rate (%) | p-value vs placebo | Median | p-value vs placebo | Mean | p-value vs placebo |
|---|---|---|---|---|---|---|---|---|
| Placebo-controlled, double-blind study phase ||||||||||
| 1 | 0 (Placebo) | 15 | 100.0 | | 0 | | 0 | |
| 1 | 2,500 | 16 | 100.0 | | 0 | 1.00 | 0 | |
| 1 | 5,000 | 15 | 100.0 | | 0 | 1.00 | 0 | |
| 1 | 10,000 | 14 | 100.0 | | 0 | 0.34 | −0.21 | 0.31 |
| Open-label study phase ||||||||||
| 2 | 10,000 | 44 | | | 0 | | −0.07 | |
| 3 | 10,000 | 24 | | | 0 | | 0 | |
| 4 | 10,000 | 3 | | | 0 | | 0 | |
| 5 | 10,000 | 2 | | | 0 | | 0 | |

TABLE 12

Change from baseline (except success rate) at the 30-day study visit
Function

| Treatment cycle | Incremental dose | n | Protocol-defined success rate (%) | p-value vs placebo | Median | p-value vs placebo | Mean | p-value vs placebo |
|---|---|---|---|---|---|---|---|---|
| Placebo-controlled, double-blind study phase ||||||||||
| 1 | 0 (Placebo) | 15 | 26.7 | | 10.0 | | 11.20 | |
| 1 | 2,500 | 16 | 25.0 | 1.00 | 13.0 | 0.72 | 12.10 | 0.73 |
| 1 | 5,000 | 15 | 46.7 | 0.45 | 18.0 | 0.17 | 16.40 | 0.11 |
| 1 | 10,000 | 14 | 42.9 | 0.45 | 19.0 | 0.06 | 17.79 | 0.04 |
| Open-label study phase ||||||||||
| 2 | 10,000 | 44 | | | 22.0 | | 20.50 | |
| 3 | 10,000 | 24 | | | 25.5 | | 22.88 | |
| 4 | 10,000 | 3 | | | 26.0 | | 23.67 | |
| 5 | 10,000 | 2 | | | 20.5 | | 20.50 | |

TABLE 13

Change from baseline (except success rate) at the 30-day study visit
Pain

| Treatment cycle | Incremental dose | n | Protocol-defined success rate (%) | p-value vs placebo | Median | p-value vs placebo | Mean | p-value vs placebo |
|---|---|---|---|---|---|---|---|---|
| Placebo-controlled, double-blind study phase | | | | | | | | |
| 1 | 0 (Placebo) | 15 | 86.7 | | 1.0 | | 1.33 | |
| 1 | 2,500 | 16 | 87.5 | 1.00 | 1.0 | 0.65 | 1.44 | 0.69 |
| 1 | 5,000 | 15 | 93.3 | 1.00 | 2.0 | 0.05 | 2.00 | 0.05 |
| 1 | 10,000 | 14 | 85.7 | 1.00 | 1.0 | 0.78 | 1.21 | 0.75 |
| Open-label study phase | | | | | | | | |
| 2 | 10,000 | 44 | | | 2.0 | | 2.16 | |
| 3 | 10,000 | 24 | | | 2.0 | | 2.13 | |
| 4 | 10,000 | 3 | | | 4.0 | | 3.00 | |
| 5 | 10,000 | 2 | | | 2.5 | | 2.50 | |

TABLE 14

Change from baseline (except success rate) at the 30-day study visit
Satisfaction

| Treatment cycle | Incremental dose | n | Protocol-defined success rate (%) | p-value vs placebo | Median | p-value vs placebo | Mean | p-value vs placebo |
|---|---|---|---|---|---|---|---|---|
| Placebo-controlled, double-blind study phase | | | | | | | | |
| 1 | 0 (Placebo) | 15 | 53.3 | | | | | |
| 1 | 2,500 | 16 | 68.8 | 0.47 | | | | |
| 1 | 5,000 | 15 | 66.7 | 0.71 | | | | |
| 1 | 10,000 | 14 | 78.6 | 0.25 | | | | |
| Open-label study phase | | | | | | | | |
| 2 | 10,000 | | | | | | | |
| 3 | 10,000 | | | | | | | |
| 4 | 10,000 | | | | | | | |
| 5 | 10,000 | | | | | | | |

TABLE 15

Open-label phase change from baseline at the 30-day study visit
Active elevation
Open-label study phase

| Treatment cycle | Randomization treatment arm | n | Mean change from baseline (degrees) | p-value |
|---|---|---|---|---|
| 2 | 0 (Placebo) | 13 | 28.3 | <.0001 |
| 2 | 2,500 | 12 | 32.4 | <.0001 |
| 2 | 5,000 | 10 | 33.6 | 0.0007 |
| 2 | 10,000 | 10 | 43.6 | <.0001 |
| 3 | 0 (Placebo) | 7 | 34.3 | 0.0008 |
| 3 | 2,500 | 7 | 34.1 | 0.0023 |
| 3 | 5,000 | 4 | 43.8 | 0.0089 |
| 3 | 10,000 | 6 | 47.3 | 0.0002 |

TABLE 16

Open-label phase change from baseline at the 30-day study visit
Passive elevation
Open-label study phase

| Treatment cycle | Randomization treatment arm | n | Mean change from baseline (degrees) | p-value |
|---|---|---|---|---|
| 2 | 0 (Placebo) | 13 | 29.2 | 0.0001 |
| 2 | 2,500 | 12 | 23.9 | 0.0002 |
| 2 | 5,000 | 10 | 30.4 | 0.0022 |
| 2 | 10,000 | 10 | 26.9 | 0.0002 |
| 3 | 0 (Placebo) | 7 | 32.7 | 0.0008 |
| 3 | 2,500 | 7 | 25.7 | 0.0125 |
| 3 | 5,000 | 4 | 33.3 | 0.0078 |
| 3 | 10,000 | 6 | 33.6 | 0.0020 |

TABLE 17

Open-label phase change from baseline at the 30-day study visit
Active ER at side
Open-label study phase

| Treatment cycle | Randomization treatment arm | n | Mean change from baseline (degrees) | p-value |
|---|---|---|---|---|
| 2 | 0 (Placebo) | 13 | 35.2 | <.0001 |
| 2 | 2,500 | 12 | 29.0 | <.0001 |
| 2 | 5,000 | 9 | 29.8 | 0.0035 |
| 2 | 10,000 | 10 | 27.0 | 0.0014 |
| 3 | 0 (Placebo) | 7 | 38.2 | 0.0004 |
| 3 | 2,500 | 7 | 37.1 | 0.0002 |
| 3 | 5,000 | 4 | 33.7 | 0.0230 |
| 3 | 10,000 | 6 | 33.6 | 0.0015 |

TABLE 18

Open-label phase change from baseline at the 30-day study visit
Passive ER at side
Open-label study phase

| Treatment cycle | Randomization treatment arm | n | Mean change from baseline (degrees) | p-value |
|---|---|---|---|---|
| 2 | 0 (Placebo) | 13 | 39.6 | <.0001 |
| 2 | 2,500 | 12 | 31.3 | 0.0005 |
| 2 | 5,000 | 9 | 32.6 | 0.0008 |
| 2 | 10,000 | 10 | 39.1 | 0.0007 |
| 3 | 0 (Placebo) | 7 | 41.1 | 0.0064 |
| 3 | 2,500 | 7 | 26.9 | 0.0064 |
| 3 | 5,000 | 4 | 32.2 | 0.0259 |
| 3 | 10,000 | 6 | 41.3 | 0.0030 |

TABLE 19

Open-label phase change from baseline at the 30-day study visit
IR spinal level
Open-label study phase

| Treatment cycle | Randomization treatment arm | n | Mean change from baseline (degrees) | p-value |
|---|---|---|---|---|
| 2 | 0 (Placebo) | 13 | 5.2 | <.0001 |
| 2 | 2,500 | 12 | 4.3 | 0.0043 |
| 2 | 5,000 | 9 | 5.7 | 0.0013 |
| 2 | 10,000 | 10 | 5.7 | 0.0010 |
| 3 | 0 (Placebo) | 7 | 5.0 | 0.0067 |
| 3 | 2,500 | 7 | 4.7 | 0.0080 |
| 3 | 5,000 | 4 | 8.8 | 0.0635 |
| 3 | 10,000 | 6 | 4.8 | 0.0081 |

TABLE 20

Open-label phase change from baseline at the 30-day study visit
Passive ER at 90°
Open-label study phase

| Treatment cycle | Randomization treatment arm | n | Mean change from baseline (degrees) | p-value |
|---|---|---|---|---|
| 2 | 0 (Placebo) | 13 | 26.4 | <.0001 |
| 2 | 2,500 | 12 | 17.3 | 0.0056 |
| 2 | 5,000 | 9 | 28.8 | 0.0012 |
| 2 | 10,000 | 10 | 23.7 | 0.0060 |
| 3 | 0 (Placebo) | 7 | 30.4 | 0.0030 |
| 3 | 2,500 | 7 | 16.0 | 0.0491 |
| 3 | 5,000 | 4 | 29.2 | 0.0157 |
| 3 | 10,000 | 6 | 19.0 | 0.0058 |

TABLE 21

Open-label phase change from baseline at the 30-day study visit
Strength
Open-label study phase

| Treatment cycle | Randomization treatment arm | n | Mean change from baseline | p-value |
|---|---|---|---|---|
| 2 | 0 (Placebo) | 13 | 0 | |
| 2 | 2,500 | 12 | −0.3 | 0.3388 |
| 2 | 5,000 | 9 | 0.2 | 0.3466 |
| 2 | 10,000 | 10 | 0 | |
| 3 | 0 (Placebo) | 7 | 0 | |
| 3 | 2,500 | 7 | −0.3 | 0.3559 |
| 3 | 5,000 | 4 | 0 | |
| 3 | 10,000 | 6 | 0 | |

TABLE 22

Open-label phase change from baseline at the 30-day study visit
Stability
Open-label study phase

| Treatment cycle | Randomization treatment arm | n | Mean change from baseline | p-value |
|---|---|---|---|---|
| 2 | 0 (Placebo) | 13 | 0 | |
| 2 | 2,500 | 12 | −0.3 | 0.3388 |
| 2 | 5,000 | 9 | 0 | |
| 2 | 10,000 | 10 | 0 | |
| 3 | 0 (Placebo) | 7 | 0 | |
| 3 | 2,500 | 7 | 0 | |
| 3 | 5,000 | 4 | 0 | |
| 3 | 10,000 | 6 | 0 | |

TABLE 23

Open-label phase change from baseline at the 30-day study visit
Function
Open-label study phase

| Treatment cycle | Randomization treatment arm | n | Mean change from baseline | p-value |
|---|---|---|---|---|
| 2 | 0 (Placebo) | 13 | 20.6 | <.0001 |
| 2 | 2,500 | 12 | 21.0 | <.0001 |
| 2 | 5,000 | 9 | 18.4 | 0.0006 |
| 2 | 10,000 | 10 | 21.6 | <.0001 |
| 3 | 0 (Placebo) | 7 | 22.7 | 0.0037 |
| 3 | 2,500 | 7 | 23.1 | <.0001 |
| 3 | 5,000 | 4 | 15.8 | 0.1151 |
| 3 | 10,000 | 6 | 27.5 | 0.0002 |

TABLE 24

Open-label phase change from baseline at the 30-day study visit
Pain
Open-label study phase

| Treatment cycle | Randomization treatment arm | n | Mean change from baseline | p-value |
|---|---|---|---|---|
| 2 | 0 (Placebo) | 13 | 2 | <.0001 |
| 2 | 2,500 | 12 | 2.3 | <.0001 |
| 2 | 5,000 | 9 | 2.4 | <.0001 |
| 2 | 10,000 | 10 | 1.9 | 0.0007 |
| 3 | 0 (Placebo) | 7 | 1.9 | 0.0004 |
| 3 | 2,500 | 7 | 2.3 | 0.0007 |
| 3 | 5,000 | 4 | 2.0 | 0.0917 |
| 3 | 10,000 | 6 | 2.3 | 0.0001 |

TABLE 25

Change from contralateral shoulder baseline for the 30-day study visit
Active elevation

| Treatment cycle | Randomization treatment arm | n | Mean change from contralateral baseline (degrees) | p-value vs placebo |
|---|---|---|---|---|
| Placebo-controlled, double-blind study phase | | | | |
| 1 | 0 (Placebo) | 12 | −35.6 | |
| 1 | 2,500 | 10 | −33.8 | 0.8269 |
| 1 | 5,000 | 12 | −38.0 | 0.7652 |
| 1 | 10,000 | 12 | −26.9 | 0.3834 |
| Open-label study phase | | | | Lower limit of one-sided 90% CI |
| 2 | 0 (Placebo) | 10 | −13.9 | −20.9 |
| 2 | 2,500 | 8 | −18.1 | −24.2 |
| 2 | 5,000 | 8 | −24.1 | −29.6 |
| 2 | 10,000 | 8 | −12.4 | −18.5 |
| 3 | 0 (Placebo) | 4 | −13.5 | −25.5 |
| 3 | 2,500 | 5 | −15.2 | −20.7 |
| 3 | 5,000 | 3 | −10.0 | −10.0 |
| 3 | 10,000 | 5 | −9.0 | −20.4 |

TABLE 26

Change from contralateral shoulder baseline for the 30-day study visit
Passive elevation

| Treatment cycle | Randomization treatment arm | n | Mean change from contralateral baseline (degrees) | p-value vs placebo |
|---|---|---|---|---|
| Placebo-controlled, double-blind study phase | | | | |
| 1 | 0 (Placebo) | 12 | −24.4 | |
| 1 | 2,500 | 10 | −30.6 | 0.3050 |
| 1 | 5,000 | 12 | −26.8 | 0.6892 |
| 1 | 10,000 | 12 | −25.3 | 0.9127 |
| Open-label study phase | | | | Lower limit of one-sided 90% CI |
| 2 | 0 (Placebo) | 10 | −7.8 | −11.9 |
| 2 | 2,500 | 8 | −21.5 | −27.7 |
| 2 | 5,000 | 8 | −14.1 | −20.2 |
| 2 | 10,000 | 8 | −17.3 | −22.9 |
| 3 | 0 (Placebo) | 4 | −5.0 | −12.9 |
| 3 | 2,500 | 5 | −19.2 | −24.2 |
| 3 | 5,000 | 3 | −7.0 | −15.2 |
| 3 | 10,000 | 5 | −9.6 | −18.4 |

TABLE 27

Change from contralateral shoulder baseline for the 30-day study visit
Active ER at side

| Treatment cycle | Randomization treatment arm | n | Mean change from contralateral baseline (degrees) | p-value vs placebo |
|---|---|---|---|---|
| Placebo-controlled, double-blind study phase | | | | |
| 1 | 0 (Placebo) | 12 | −35.8 | |
| 1 | 2,500 | 10 | −40.8 | 0.5358 |
| 1 | 5,000 | 12 | −20.0 | 0.0120 |
| 1 | 10,000 | 12 | −19.8 | 0.0255 |
| Open-label study phase | | | | Lower limit of one-sided 90% CI |
| 2 | 0 (Placebo) | 10 | −15.6 | −21.8 |
| 2 | 2,500 | 8 | −32.1 | −39.2 |
| 2 | 5,000 | 7 | −9.6 | −13.7 |
| 2 | 10,000 | 8 | −15.6 | −23.3 |
| 3 | 0 (Placebo) | 4 | −15.5 | −29.9 |
| 3 | 2,500 | 5 | −26.8 | −42.1 |
| 3 | 5,000 | 3 | −18.0 | −24.6 |
| 3 | 10,000 | 5 | −6.8 | −12.7 |

TABLE 28

Change from contralateral shoulder baseline for the 30-day study visit
Passive ER at side

| Treatment cycle | Randomization treatment arm | n | Mean change from contralateral baseline (degrees) | p-value vs placebo |
|---|---|---|---|---|
| Placebo-controlled, double-blind study phase | | | | |
| 1 | 0 (Placebo) | 12 | −35.7 | |
| 1 | 2,500 | 10 | −37.0 | 0.8546 |

TABLE 28-continued

Change from contralateral shoulder baseline for the 30-day study visit
Passive ER at side

| Treatment cycle | Randomization treatment arm | n | Mean change from contralateral baseline (degrees) | |
|---|---|---|---|---|
| 1 | 5,000 | 12 | −27.5 | 0.2663 |
| 1 | 10,000 | 12 | −26.3 | 0.2017 |
| Open-label study phase | | | | |
| | | | | Lower limit of one-sided 90% CI |
| 2 | 0 (Placebo) | 10 | −11.0 | −16.9 |
| 2 | 2,500 | 8 | −28.1 | −37.3 |
| 2 | 5,000 | 7 | −16.4 | −25.5 |
| 2 | 10,000 | 8 | −23.3 | −30.8 |
| 3 | 0 (Placebo) | 4 | −2.5 | −10.3 |
| 3 | 2,500 | 5 | −21.0 | −32.2 |
| 3 | 5,000 | 3 | −18.0 | −24.6 |
| 3 | 10,000 | 5 | −20.2 | −27.8 |

TABLE 29

Change from contralateral shoulder baseline for the 30-day study visit
IR spinal level

| Treatment cycle | Randomization treatment arm | n | Mean change from contralateral baseline (degrees) | |
|---|---|---|---|---|
| Placebo-controlled, double-blind study phase | | | | |
| | | | | p-value vs placebo |
| 1 | 0 (Placebo) | 12 | −6.9 | |
| 1 | 2,500 | 10 | −5.8 | 0.4766 |
| 1 | 5,000 | 12 | −4.5 | 0.0917 |
| 1 | 10,000 | 12 | −7.3 | 0.7881 |
| Open-label study phase | | | | |
| | | | | Lower limit of one-sided 90% CI |
| 2 | 0 (Placebo) | 10 | −3.7 | −5.9 |
| 2 | 2,500 | 8 | −3.0 | −5.7 |
| 2 | 5,000 | 7 | −3.3 | −4.8 |
| 2 | 10,000 | 8 | −5.4 | −7.5 |
| 3 | 0 (Placebo) | 4 | −3.3 | −6.6 |
| 3 | 2,500 | 5 | −4.6 | −7.1 |
| 3 | 5,000 | 3 | −1.0 | −2.1 |
| 3 | 10,000 | 5 | −5.6 | −7.5 |

TABLE 30

Change from contralateral shoulder baseline for the 30-day study visit
Passive ER at 90°

| Treatment cycle | Randomization treatment arm | n | Mean change from contralateral baseline (degrees) | |
|---|---|---|---|---|
| Placebo-controlled, double-blind study phase | | | | |
| | | | | p-value vs placebo |
| 1 | 0 (Placebo) | 12 | −16.2 | |
| 1 | 2,500 | 10 | −22.1 | 0.4676 |
| 1 | 5,000 | 12 | −20.9 | 0.4260 |
| 1 | 10,000 | 12 | −13.6 | 0.6256 |
| Open-label study phase | | | | |
| | | | | Lower limit of one-sided 90% CI |
| 2 | 0 (Placebo) | 10 | −1.9 | −5.7 |
| 2 | 2,500 | 8 | −11.6 | −20.5 |
| 2 | 5,000 | 7 | −14.1 | −19.6 |
| 2 | 10,000 | 8 | −6.0 | −13.2 |
| 3 | 0 (Placebo) | 4 | 0.5 | −6.2 |
| 3 | 2,500 | 5 | −11.2 | −21.9 |
| 3 | 5,000 | 3 | −1.6 | −27.3 |
| 3 | 10,000 | 5 | −6.6 | −14.6 |

TABLE 31

Change from contralateral shoulder baseline for the 30-day study visit
Strength

| Treatment cycle | Randomization treatment arm | n | Mean change from contralateral baseline (degrees) | |
|---|---|---|---|---|
| Placebo-controlled, double-blind study phase | | | | |
| | | | | p-value vs placebo |
| 1 | 0 (Placebo) | 12 | 0 | |
| 1 | 2,500 | 10 | 0 | |
| 1 | 5,000 | 12 | 0 | |
| 1 | 10,000 | 12 | −0.5 | 0.1775 |
| Open-label study phase | | | | |
| | | | | Lower limit of one-sided 90% CI |
| 2 | 0 (Placebo) | 10 | 0 | 0 |
| 2 | 2,500 | 8 | 0 | 0 |
| 2 | 5,000 | 7 | 0 | 0 |
| 2 | 10,000 | 8 | 0 | 0 |
| 3 | 0 (Placebo) | 4 | 0 | 0 |
| 3 | 2,500 | 5 | −0.4 | −1.0 |
| 3 | 5,000 | 3 | 0 | 0 |
| 3 | 10,000 | 5 | 0 | 0 |

TABLE 32

Change from contralateral shoulder baseline for the 30-day study visit
Stability

| Treatment cycle | Randomization treatment arm | n | Mean change from contralateral baseline (degrees) | |
|---|---|---|---|---|
| Placebo-controlled, double-blind study phase | | | | |
| | | | | p-value vs placebo |
| 1 | 0 (Placebo) | 12 | 0 | |
| 1 | 2,500 | 10 | 0 | |
| 1 | 5,000 | 12 | 0 | |
| 1 | 10,000 | 12 | −0.3 | 0.3282 |
| Open-label study phase | | | | |
| | | | | Lower limit of one-sided 90% CI |
| 2 | 0 (Placebo) | 10 | 0 | 0 |
| 2 | 2,500 | 8 | 0 | 0 |
| 2 | 5,000 | 7 | 0 | 0 |
| 2 | 10,000 | 8 | 0 | 0 |
| 3 | 0 (Placebo) | 4 | 0 | 0 |
| 3 | 2,500 | 5 | 0 | 0 |
| 3 | 5,000 | 3 | 0 | 0 |
| 3 | 10,000 | 5 | 0 | 0 |

TABLE 33

Change from contralateral shoulder baseline for the 30-day study visit
Function

| Treatment cycle | Randomization treatment arm | n | Mean change from contralateral baseline (degrees) | |
|---|---|---|---|---|
| Placebo-controlled, double-blind study phase | | | | |
| | | | | p-value vs placebo |
| 1 | 0 (Placebo) | 12 | −14.9 | |
| 1 | 2,500 | 10 | −16.3 | 0.7725 |
| 1 | 5,000 | 12 | −7.3 | 0.0546 |
| 1 | 10,000 | 12 | −10.8 | 0.3246 |
| Open-label study phase | | | | |
| | | | | Lower limit of one-sided 90% CI |
| 2 | 0 (Placebo) | 10 | −4.6 | −7.1 |
| 2 | 2,500 | 8 | −9.5 | −12.4 |
| 2 | 5,000 | 7 | −5.4 | −8.7 |
| 2 | 10,000 | 8 | −8.1 | −11.9 |
| 3 | 0 (Placebo) | 4 | −3.0 | −4.8 |
| 3 | 2,500 | 5 | −7.0 | −9.9 |
| 3 | 5,000 | 3 | −2.7 | −4.9 |
| 3 | 10,000 | 5 | −2.6 | −4.6 |

TABLE 34

Change from contralateral shoulder baseline for the 30-day study visit
Pain

| Treatment cycle | Randomization treatment arm | n | Mean change from contralateral baseline (degrees) | |
|---|---|---|---|---|
| Placebo-controlled, double-blind study phase | | | | |
| | | | | p-value vs placebo |
| 1 | 0 (Placebo) | 12 | −1.5 | |
| 1 | 2,500 | 10 | −1.8 | 0.4508 |
| 1 | 5,000 | 12 | −0.8 | 0.0580 |
| 1 | 10,000 | 12 | −1.5 | 1.0000 |
| Open-label study phase | | | | |
| | | | | Lower limit of one-sided 90% CI |
| 2 | 0 (Placebo) | 10 | −0.8 | −1.1 |
| 2 | 2,500 | 8 | −0.8 | −1.0 |
| 2 | 5,000 | 7 | −0.9 | −1.1 |
| 2 | 10,000 | 8 | −0.9 | −1.4 |
| 3 | 0 (Placebo) | 4 | −0.8 | −1.2 |
| 3 | 2,500 | 5 | −0.6 | −1.0 |
| 3 | 5,000 | 3 | −0.7 | −1.3 |
| 3 | 10,000 | 5 | −0.8 | −1.1 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating adhesive capsulitis in a subject in need of such treatment comprising delivering an effective amount of collagenase to collagenous adhesions in the shoulder, wherein the collagenase is obtained from *Clostridium histolyticum*, wherein the subject is a human patient and wherein the method comprises injecting collagenase to the patient in a dose of about 10,000 ABC units.

2. The method according to claim 1, wherein the collagenase is injected in a liquid pharmaceutically acceptable carrier wherein the volume of liquid injected is 0.5 ml or less.

3. The method according to claim 1, wherein the collagenase comprises collagenase I and collagenase II.

4. The method according to claim 2, wherein the injection is delivered in a single injection between the interval of the deltoid and pectoral muscles.

5. The method according to claim 1, wherein the patient is characterized by an active forward elevation of only 90 degrees and an active external rotation of less than 50 degrees.

6. The method according to claim 1, wherein after one month of receiving at least one administration of collagenase, the patient achieves an active external rotation of greater than 15°, as compared to baseline.

7. The method of claim 1, comprising administering one or two injections of about 10,000 ABC units of collagenase.

8. A method of treating adhesive capsulitis in a subject in need of such treatment comprising injecting collagenase in a dose of about 10,000 ABC units to collagenous adhesions in the shoulder of the subject, wherein the collagenase is injected in a liquid pharmaceutically acceptable carrier, wherein the volume of liquid injected is 0.5 ml or less, and wherein the collagenase is obtained from *Clostridium histolyticum*.

* * * * *

UNITED STATES PATENT AND TRADEMARK OFFICE
CERTIFICATE OF CORRECTION

PATENT NO. : 8,323,643 B2
APPLICATION NO. : 12/266090
DATED : December 4, 2012
INVENTOR(S) : Marie A. Badalamente and Edward Wang It is certified that error appears in the above-identified patent and that said Letters Patent is hereby corrected as shown below:

In Column 1, Lines 16-18, under GOVERNMENT SUPPORT, please replace with the following paragraph
-- This invention was made with government support under grant number RR010710 awarded by the National Institute of Health. The government has certain rights in the invention. --

Signed and Sealed this
Fifth Day of March, 2013

Teresa Stanek Rea
*Acting Director of the United States Patent and Trademark Office*